US012427328B2

(12) United States Patent
Chon et al.

(10) Patent No.: US 12,427,328 B2
(45) Date of Patent: Sep. 30, 2025

(54) AUTOMATED CONDITION-BASED SUPPRESSION OF CPR ARTIFACTS IN ECG DATA

(71) Applicant: UNIVERSITY OF CONNECTICUT, Farmington, CT (US)

(72) Inventors: Ki H. Chon, Mansfield, CT (US); Shirin Hajeb, Vernon, CT (US)

(73) Assignee: UNIVERSITY OF CONNECTICUT, Farmington, CT (US)

( * ) Notice: Subject to any disclaimer, the term of this patent is extended or adjusted under 35 U.S.C. 154(b) by 395 days.

(21) Appl. No.: 18/050,778

(22) Filed: Oct. 28, 2022

(65) Prior Publication Data

US 2023/0138815 A1    May 4, 2023

Related U.S. Application Data

(60) Provisional application No. 63/272,705, filed on Oct. 28, 2021.

(51) Int. Cl.
*A61N 1/39* (2006.01)
*A61B 5/24* (2021.01)

(52) U.S. Cl.
CPC . *A61N 1/39* (2013.01); *A61B 5/24* (2021.01)

(58) Field of Classification Search
CPC ........ A61N 1/39; A61N 1/39044; A61B 5/24; A61B 5/725
See application file for complete search history.

(56) References Cited

U.S. PATENT DOCUMENTS

| | | | | |
|---|---|---|---|---|
| 2015/0297107 | A1* | 10/2015 | Sullivan | A61B 5/24 600/523 |
| 2018/0001100 | A1* | 1/2018 | Gehman | A61B 5/316 |
| 2019/0001144 | A1* | 1/2019 | Liu | A61N 1/3925 |
| 2019/0105504 | A1* | 4/2019 | Liu | A61B 5/316 |

OTHER PUBLICATIONS

Hajeb-Mohammadalipour, S., Cascella, A., Valentine, M., & Chon, K. H. (2021). Automated Condition-Based Suppression of the CPR Artifact in ECG Data to Make a Reliable Shock Decision for AEDs during CPR. Sensors, 21(24), 8210. https://doi.org/10.3390/s21248210 (Year: 2021).*
Electronics Tutorials. "Band Stop Filters are Called Reject Filters." Basic Electronics Tutorials, May 22, 2018, www.electronics-tutorials.ws/filter/band-stop-filter.html. (Year: 2018).*
"Notch Filter." Www.mathworks.com, www.mathworks.com/discovery/notch-filter.html.*

* cited by examiner

*Primary Examiner* — Paula J Stice
(74) *Attorney, Agent, or Firm* — Lisa Mueller; Rick L. Abegglen; Casimir Jones SC

(57) ABSTRACT

Methods, systems, and apparatuses are described for automated external defibrillation for determining shock/no-shock decisions based on ECG readings taken when a patient is undergoing cardiopulmonary resuscitation (CPR). A device may filter an ECG signal of a patient to reduce artifacts from the signal caused by CPR being performed on the patient. The device may use the filtered ECG signal to determine whether to deliver a therapeutic shock to a patient even if the patient is undergoing CPR.

30 Claims, 11 Drawing Sheets

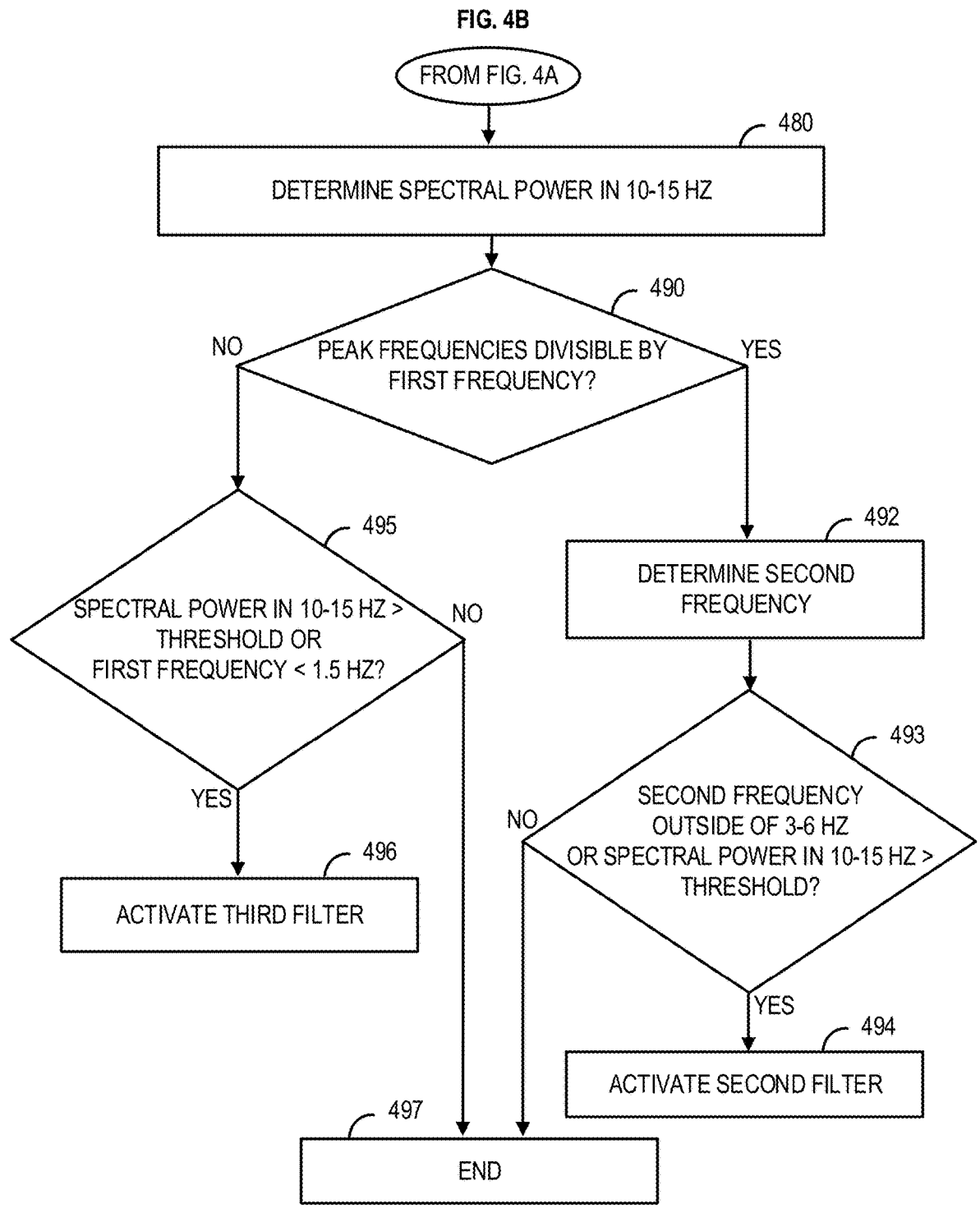

AUTOMATED CONDITION-BASED SUPPRESSION OF CPR ARTIFACTS IN ECG DATA

CROSS REFERENCE TO RELATED PATENT APPLICATION

This Application claims priority to U.S. Provisional Application No. 63/272,705, filed Oct. 28, 2021, which is herein incorporated by reference in its entirety.

BACKGROUND

Out of hospital cardiac arrest (OHCA) affects more than 325,000 people in the United States each year. This occurs either due to shockable rhythms, such as rapid ventricular tachycardia (RVT) and ventricular fibrillation (VF), or non-shockable rhythms such as asystole and pulseless electrical activity (PEA). Two-thirds of OHCAs start as a non-shockable rhythm. The most effective treatment for non-shockable rhythms is cardiopulmonary resuscitation (CPR). For shockable RVT and VF, applying an electrical shock with an automated external defibrillator (AED) in conjunction with CPR is critical to reset heart activity.

Conventional AEDs use rhythm classification logic/algorithms to automatically make shock versus no-shock decisions. However, during CPR, chest compressions (CCs) induce severe artifacts in the electrocardiogram (ECG) that can destroy the morphology of the waveforms from which rhythm classification and shock/no-shock decisions are made. For example, CPR artifacts based on shockable rhythms can resemble a regular rhythm with a rate equal to CCs. Consequently, an AED's arrhythmia detection algorithm may be fooled by the rhythmicity of CPR artifacts and make an incorrect non-shock decision for a shockable rhythm. Conversely, CCs may also add fast and disorganized components to non-shockable rhythms which may lead to a misclassification of a non-shockable rhythm as shockable. Hence, to reduce inaccurate shock versus non-shock classifications, conventional AEDs require pre-shock CPR interruptions to acquire artifact-free ECGs from which reliable rhythm analyses may be performed. However, these interruptions may increase the severity of the ischemic injury both to the heart and to the brain. Moreover, resuming CPR after an interruption does not promptly lead to the return of spontaneous circulation (ROSC). Consequently, CPR interruptions reduce the survival rate of OHCA patients.

Various filtering methods using signal processing techniques have been developed during the last two decades to suppress CPR artifacts. The majority of these techniques are based on Kalman filters, different adaptive filtering methods such as least mean square (LMS), the enhanced adaptive method, and recursive least-squares (RLS). However, these techniques require a patient ECG signal in addition to one or more reference signals (such as chest pressure, chest displacement, chest acceleration, compression depth, or thoracic impedance) in order to make a rhythm classification and a shock/no-shock decision. Unfortunately, most AEDs in the marketplace do not have hardware to capture such reference signals.

SUMMARY

It is understood that both the following general description and the following detailed description are exemplary and explanatory only and are not restrictive.

Methods, systems, and apparatuses are described for automated external defibrillation for making shock/no-shock decisions based on ECG readings taken while a patient is undergoing CPR. Specifically, a condition-based filtering method may be applied to a patient's ECG signal to filter CPR artifacts from the ECG. The condition-based filtering method may comprise a plurality of stop-band filters, wherein each filter is set as active or non-active according to frequency-wise locations in a power spectrum of the ECG signal. An AED may generate an alert to affect application of a therapeutic shock to the patient based on a shock recommendation determined following the condition-based processing of the ECG signal to suppress CPR-related artifacts.

In an embodiment, are methods comprising receiving, by a computing device, an ECG signal associated with a patient, wherein the ECG signal comprises one or more artifacts, determining, based on the ECG signal, a first stop-band filter, determining, based on the first stop-band filter and the ECG signal, a filtered ECG signal, determining, based on a first condition associated with the filtered ECG signal, a second condition associated with the filtered ECG signal, determining, based on the second condition satisfying a threshold, a second stop-band filter, determining, based on the second stop-band filter and the filtered ECG signal, a modified ECG signal, and determining, based on the modified ECG signal, to initiate a therapeutic shock to the patient.

In an embodiment, are methods comprising receiving, by a computing device, an ECG signal associated with a patient, wherein the ECG signal comprises one or more artifacts, determining, based on the ECG signal, a stop-band filter, determining, based on the stop-band filter and the ECG signal, a filtered ECG signal, determining, based on a first condition associated with the filtered ECG signal, a second condition associated with the filtered ECG signal, determining, based on the second condition not satisfying a threshold, a modified ECG signal, and determining, based on the modified ECG signal, to initiate a therapeutic shock to the patient.

Additional advantages will be set forth in part in the description which follows or may be learned by practice. The advantages will be realized and attained by means of the elements and combinations particularly pointed out in the appended claims. It is to be understood that both the foregoing general description and the following detailed description are exemplary and explanatory only and are not restrictive.

BRIEF DESCRIPTION OF THE DRAWINGS

The accompanying drawings, which are incorporated in and constitute a part of the present description serve to explain the principles of the methods and systems described herein. To easily identify the discussion of any particular element or act, the most significant digit or digits in a reference number may refer to the figure number in which that element is first introduced.

FIGS. 4A-4B show a flowchart of an example method.

DETAILED DESCRIPTION

Figure 1:
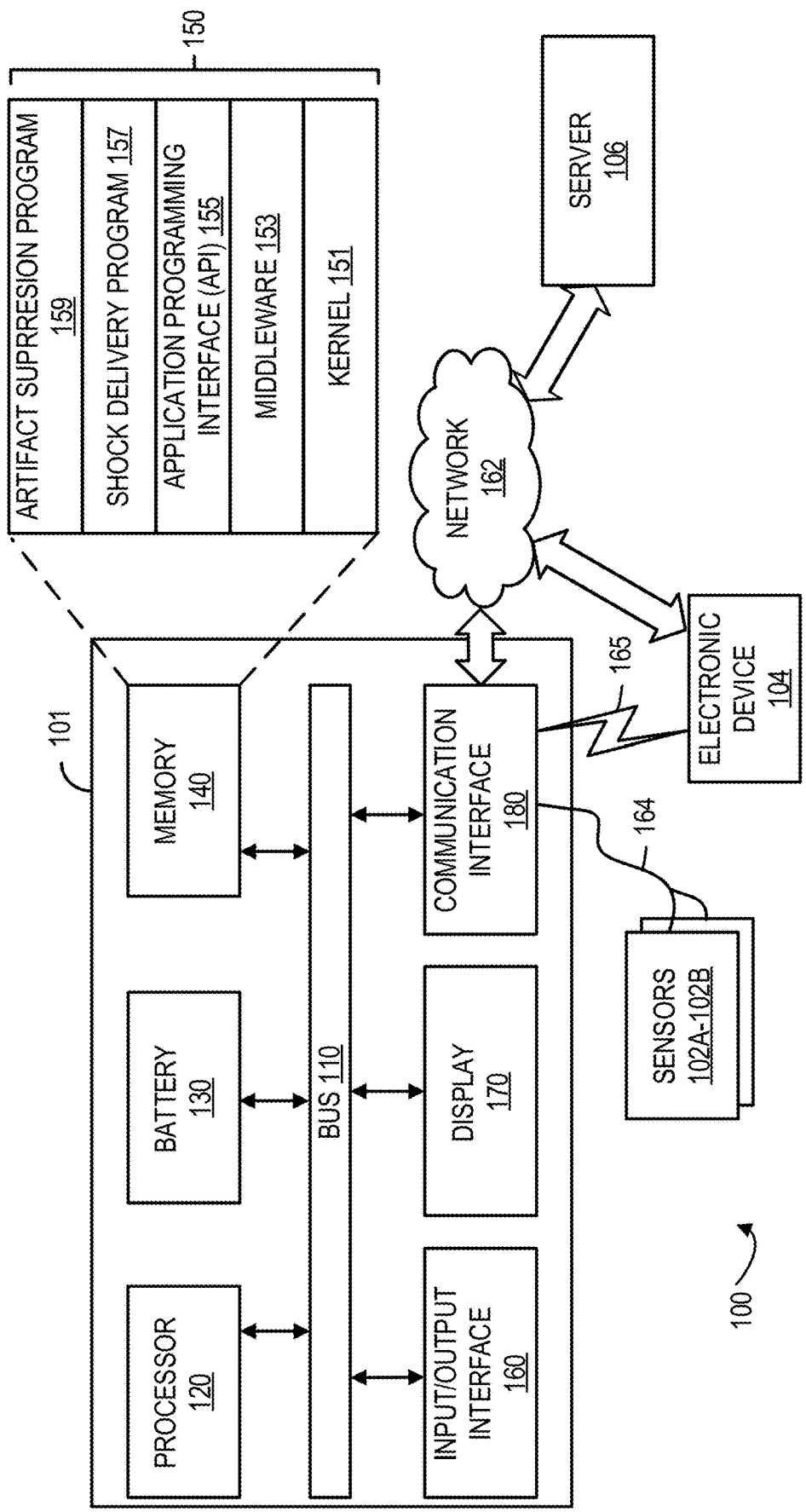
FIG. 1 shows an example system environment.

Before the present methods and systems are disclosed and described, it is to be understood that the methods and systems are not limited to specific methods, specific components, or to particular implementations. It is also to be understood that the terminology used herein is for the purpose of describing particular embodiments only and is not intended to be limiting.

As used in the specification and the appended claims, the singular forms "a," "an" and "the" include plural referents unless the context clearly dictates otherwise.

Throughout the description and claims of this specification, the word "comprise" and variations of the word, such as "comprising" and "comprises," means "including but not limited to," and is not intended to exclude, for example, other components, integers or steps. "Exemplary" means "an example of" and is not intended to convey an indication of a preferred or ideal embodiment. "Such as" is not used in a restrictive sense, but for explanatory purposes.

Disclosed are components (e.g., apparatuses) that can be used to perform the disclosed methods and can be part of the disclosed systems. These and other components are disclosed herein, and it is understood that when combinations, subsets, interactions, groups, etc. of these components are disclosed that while specific reference of each various individual and collective combinations and permutation of these may not be explicitly disclosed, each is specifically contemplated and described herein, for all methods and systems. This applies to all aspects of this application including, but not limited to, steps in disclosed methods. Thus, if there are a variety of additional steps that can be performed it is understood that each of these additional steps can be performed with any specific embodiment or combination of embodiments of the disclosed methods.

The present methods and systems may be understood more readily by reference to the following detailed description of example embodiments and the examples included therein and to the Figures and their previous and following description.

As will be appreciated by one skilled in the art, the methods and systems may take the form of an entirely hardware embodiment, an entirely software embodiment, or an embodiment combining software and hardware aspects. Furthermore, the methods and systems may take the form of a computer program product on a computer-readable storage medium (e.g., non-transitory) having processor-executable instructions (e.g., computer software) embodied in the storage medium. More particularly, the present methods and systems may take the form of web-implemented computer software. Any suitable computer-readable storage medium may be utilized including hard disks, CD-ROMs, optical storage devices, magnetic storage devices, memresistors, Non-Volatile Random Access Memory (NVRAM), flash memory, or a combination thereof.

Embodiments of the methods and systems are described below with reference to block diagrams and flowchart illustrations of methods, systems, apparatuses and computer program products. It will be understood that each block of the block diagrams and flowchart illustrations, and combinations of blocks in the block diagrams and flowchart illustrations, respectively, can be implemented by computer program instructions. These processor-executable instructions may be loaded onto a general purpose computer, special purpose computer, or other programmable data processing apparatus to produce a machine, such that the instructions which execute on the computer or other programmable data processing apparatus create a means for implementing the functions specified in the flowchart block or blocks.

These processor-executable instructions may also be stored in a computer-readable memory that can direct a computer or other programmable data processing apparatus to function in a particular manner, such that the instructions stored in the computer-readable memory produce an article of manufacture including computer-readable instructions for implementing the function specified in the flowchart block or blocks. The processor-executable instructions may also be loaded onto a computer or other programmable data processing apparatus to cause a series of operational steps to be performed on the computer or other programmable apparatus to produce a computer-implemented process such that the instructions that execute on the computer or other programmable apparatus provide steps for implementing the functions specified in the flowchart block or blocks.

Accordingly, blocks of the block diagrams and flowchart illustrations support combinations of means for performing the specified functions, combinations of steps for performing the specified functions and program instruction means for performing the specified functions. It will also be understood that each block of the block diagrams and flowchart illustrations, and combinations of blocks in the block diagrams and flowchart illustrations, can be implemented by special purpose hardware-based computer systems that perform the specified functions or steps, or combinations of special purpose hardware and computer instructions.

Hereinafter, various embodiments of the present disclosure will be described with reference to the accompanying drawings. As used herein, the term "user," may indicate the person operating the defibrillator. In addition, as used herein, the term "patient," may indicate a person that is being monitored by the defibrillator and undergoing CPR.

Methods and systems are described for making shock/no-shock decisions for automated external defibrillation based on electrocardiogram (ECG) readings taken while a patient is undergoing CPR. Specifically, a condition-based filtering method may be applied to a patient's ECG signal to filter CPR-related artifacts from the ECG signal. The condition-based filtering method may comprise a plurality of stop-band filters, wherein each filter may be set as active or non-active according to frequency-wise locations in a power spectrum of the ECG signal. An initial signal associated with a patient may be received. The signal may comprise an electrocardiogram (ECG) signal, including artifacts associated with CPR being performed on the patient. The initial signal may be preprocessed by applying a filter to remove electrical noise from the signal and by applying a wavelet implementation plus averaging to remove glitches. Three frequencies may be determined from the three highest frequency peaks of the power spectral density (PSD) associated with the preprocessed signal. A first stop-band filter may be determined based on a first cutoff frequency comprising a first frequency, wherein the first frequency may comprise the frequency of the three frequencies that is within a first frequency range. The first stop-band filter may be activated with the first cutoff frequency to generate a first filtered signal. For example, the first stop-band filter may be applied to the initial signal to generate the first filtered signal. A spectral power in a frequency band of the first filtered patient signal may be determined, wherein the frequency band may comprise 10-15 MHz. A second frequency may be determined based on the remaining frequency peaks of the three highest frequency peaks, of the first filtered signal. For example, the second frequency may be determined based the frequency of the remaining frequency peaks that is divisible by the first cutoff frequency. However, if both of the frequencies of the remaining frequency peaks are divisible by the first cutoff frequency, the second frequency may be determined based on the frequency of the remaining frequency peaks with the highest power. Several conditions may be analyzed to determine whether to analyze the first filtered signal, whether to analyze a second filtered signal comprising the first filtered signal that is filtered by a second stop-band filter, or whether to analyze a third filtered signal comprising the first filtered signal filtered by a third stop-band filter. For example, if the second frequency is outside of a second frequency range or the spectral power satisfies a first threshold value, the second filtered signal may be analyzed for determining whether to provide a therapeutic shock to the patient. If the spectral power satisfies the first threshold value or the first frequency satisfies a second threshold value, the third filtered signal may be analyzed to determine whether to provide a therapeutic shock to the patient. If the second frequency is within the second frequency range, the spectral power does not satisfy the first threshold value, and the first frequency does not satisfy the second threshold value, the first filtered signal may be analyzed to determine whether to provide a therapeutic shock to the patient. A classification of the patient's heart rhythm may be determined, based on the filtered signal (e.g., the first filtered signal, the second filtered signal, or the third filtered signal), and an alert may be generated based on the classification of the patient's heart rhythm. The alert may contain information or a signal indicative of a decision to cause a therapeutic shock to the patient.

Each of the elements described in the present disclosure may comprise one or more components, and names thereof may vary depending on a type of an electronic device. The electronic device according to various exemplary embodiments may include at least one of the elements described in the present disclosure. Some of the elements described herein may be omitted and/or additional other elements may be further included. Further, some of the elements of the electronic device, according to various exemplary embodiments, may be combined and constructed as a single entity, so as to equally perform functions of the corresponding elements before combination.

FIG. 1 shows an example system 100 treating a patient with cardiopulmonary issues. For example, cardiopulmonary issues may relate to a patient suffering from sudden cardiac arrest caused by a function loss of the heart. For example, system 100 may comprise a device 101 (e.g., defibrillator, automated external defibrillator, etc.) that may be configured to use one or more methods for suppression of CPR-related artifacts in patient ECG signals to facilitate a determination of whether and when to apply a defibrillating (e.g., therapeutic) shock to a patient, such as, for example, via an alert output to the device's operator according to various embodiments. Referring to FIG. 1, the system 100 comprises the device 101. The device 101 may include a bus 110, one or more processors 120, a battery 130, a memory 140, an input/output interface 160, a display 170, and a communication interface 180. In a certain examples, the device 101 may omit at least one of the aforementioned elements or may additionally include other elements. The device 101 may comprise a defibrillator. Furthermore, the device 101 may comprise a tablet computer, a laptop computer, a desktop computer, and the like.

The bus 110 may include a circuit for connecting the bus 110, the one or more processors 120, the battery 130, the memory 140, the input/output interface 160, the display 170, and/or the communication interface 180 to each other and for delivering communication (e.g., a control message and/or data) between the bus 110, the one or more processors 120, the battery 130, the memory 140, the input/output interface 160, the display 170, and/or the communication interface 180.

The one or more processors 120 may include one or more of a Central Processing Unit (CPU), an Application Processor (AP), or a Communication Processor (CP). The one or more processors 120 may control, for example, at least one of the bus 110, the battery 130, the memory 140, the input/output interface 160, the display 170, and/or the communication interface 180 of the device 101 and/or may execute an arithmetic operation or data processing for communication. For example, the one or more processors 120 may drive the display 170 and/or a speaker (not shown) to issue visual and/or audio instructions or signals, respectively to an operator of the device 101 on how to apply the pads (e.g., sensors 102A-102B) to the patient and how to initiate a therapeutic shock using the device 101. The processing (or controlling) operation of the one or more processors 120 according to various embodiments is described in detail with reference to the following drawings.

The processor-executable instructions executed by the one or more processor 120 may be stored and/or maintained by the memory 140. The memory 140 may include a volatile and/or non-volatile memory. The memory 140 may comprise random-access memory (RAM), flash memory, solid state or inertial disks, or any combination thereof. The memory 140 may store, for example, a command or data related to at least one of the bus 110, the one or more processors 120, the battery 130, the memory 140, the input/output interface 160, the display 170, and/or the communication interface 180 of the device 101. According to various examples, the memory 140 may store software and/or a program 150. The program 150 may include, for example, a kernel 151, a middleware 153, an Application Programming Interface (API) 155, a shock delivery program 157, and/or an artifact suppression program 159, or the like, configured for controlling one or more functions of the device 101 and/or an external device. At least one part of the kernel 151, middleware 153, or API 155 may be referred to as an Operating System (OS). The memory 140 may include a computer-readable recording medium (e.g., a non-transitory computer-readable medium) having a program recorded therein to perform the methods according to various embodiments by the one or more processors 120.

The kernel 151 may control or manage, for example, system resources (e.g., the bus 110, the processor 120, the battery 130, the memory 140, etc.) used to execute an operation or function implemented in other programs (e.g., the middleware 153, the API 155, the shock delivery program 157, or the artifact suppression program 159). Further, the kernel 151 may provide an interface capable of controlling or managing the system resources by accessing individual elements of the device 101 in the middleware 153, the API 155, the shock delivery program 157, or the artifact suppression program 159.

The middleware 153 may perform, for example, a mediation role, so that the API 155, the shock delivery program 157, and/or the artifact suppression program 159 can communicate with the kernel 151 to exchange data. Further, the middleware 153 may handle one or more task requests received from the shock delivery program 157 and/or the artifact suppression program 159 according to a priority. For example, the middleware 153 may assign a priority of using the system resources (e.g., the bus 110, the one or more processors 120, the battery 130, or the memory 140) of the device 101 to at least one of the shock delivery program 157 and/or the artifact suppression program 159. For example, the middleware 153 may process the one or more task requests according to the priority assigned to at least one of the application programs, and thus, may perform scheduling or load balancing on the one or more task requests.

The API 155 may include at least one interface or function (e.g., instruction), for example, for file control, window control, video processing, and/or character control, as an interface capable of controlling a function provided by the shock delivery program 157 and/or the artifact suppression program 159 in the kernel 151 or the middleware 153.

For example, the shock delivery program 157 and the artifact suppression program 159 may be independent or integrally combined, in whole or in part.

The shock delivery program 157 may comprise automated decision logic (e.g., hardware, software, firmware, etc.) that may determine if and when to deliver a therapeutic shock to the patient, or alternatively, for example, make a shock/no-shock decision, based on the analysis of the ECG signal of the patient. For example, the shock delivery program 157 may determine a classification of the patient's heart rhythm based on analyzing the ECG signal of the patient to determine the shock/no-shock decision. In certain examples, the shock delivery program 157 may determine the shock/no-shock decision based on the ECG signal of the patient during an interval when the patient is not being subject to CPR and/or without a reference signal (e.g., chest pressure, chest displacement, chest acceleration, compression depth, or thoracic impedance) that is measured concurrently (e.g., accelerometers or other sensors) with the ECG signal.

The artifact suppression program 159 may comprise logic (e.g., hardware, software, firmware, etc.) that may be implemented to perform the suppression of CPR-related artifacts in an ECG signal of the patient received from the pads/sensors 102A-102B. For example, the artifact suppression program 159 may be used to suppress the CPR-related artifacts in the ECG signal to enable the shock delivery program 157 to perform the shock/no-shock decision determinations even when a patient may be undergoing CPR during ECG signal acquisition and without the need for the concurrent acquisition of a reference signal (e.g., chest pressure, chest displacement, chest acceleration, compression depth, or thoracic impedance).

The input/output interface 160 may comprise an interface for delivering an instruction or data input from a user (e.g., an operator of the device 101) or a different external device to the different elements of the device 101. Further, the input/output interface 160 may output an instruction or data received from one or more elements of the device 101 to one or more external devices.

The display 170 may include various types of displays, for example, a Liquid Crystal Display (LCD) display, a Light Emitting Diode (LED) display, an Organic Light-Emitting Diode (OLED) display, a MicroElectroMechanical Systems (MEMS) display, or an electronic paper display. The display 170 may display, for example, a variety of contents (e.g., text, image, video, icons, symbols, etc.) to the user. For example, the display 170 may be configured to output visual instructions to the device operator on how to apply the pads/sensors 102A-102B to the patient and how to initiate a shock using the device 101. The display 170 may include a touch screen. For example, the display 170 may receive a touch, gesture, proximity, or hovering input by using a stylus pen or a part of a user's body.

The communication interface 180 may establish, for example, communication between the device 101 and one or more external devices (e.g., sensors 102A-102B, an electronic device 104, or a server 106). For example, the communication interface 170 may communicate with the one or more external devices (e.g., the electronic device 104, the server 106) by being connected to a network 162 through wireless communication or wired communication. The network 162 may include, for example, at least one of a telecommunications network, a computer network (e.g., LAN or WAN), the Internet, and/or a telephone network. The communication interface 180 may communicate with the one or more external devices (e.g., pads, sensors 102A-102B) via a wired communication interface 164 (e.g., leads).

In an example, as a cellular communication protocol, the wireless communication may use at least one of Long-Term Evolution (LTE), LTE Advance (LTE-A), Code Division Multiple Access (CDMA), Wideband CDMA (WCDMA), Universal Mobile Telecommunications System (UMTS), Wireless Broadband (WiBro), Global System for Mobile Communications (GSM), and the like. Further, the wireless communication may include, for example, a near-distance communication 165. The near-distance communications 165 may include, for example, at least one of Wireless Fidelity (WiFi), Bluetooth, Bluetooth Low Energy (BLE), Near Field Communication (NFC), Global Navigation Satellite System (GNSS), and the like. According to a usage region or a bandwidth or the like, the GNSS may include, for example, at least one of Global Positioning System (GPS), Global Navigation Satellite System (Glonass), Beidou Navigation Satellite System (hereinafter, "Beidou"), Galileo, the European global satellite-based navigation system, and the like. Hereinafter, the "GPS" and the "GNSS" may be used interchangeably in the present document. The wired communication may include, for example, at least one of Universal Serial Bus (USB), High Definition Multimedia Interface (HDMI), Recommended Standard-232 (RS-232), power-line communication, Plain Old Telephone Service (POTS), and the like. For example, the communication interface 180 may comprise or be communicably coupled to a transmitter, receiver and/or transceiver for communication with the external devices.

An electronic device 104 may communicate with the device 101 via the communication interface connection 165. The electronic device 104 may comprise, for example, a laptop computer, a mobile phone, a smart phone, a tablet computer, a smartwatch, and the like. In an example, the electronic device 104 may be configured to receive the ECG signal of the patient from the device 101 and perform a shock/no-shock determination based on the received ECG signal. The electronic device 104 may be configured to display to an operator how to apply the pads (e.g., sensors 102A-102B) to the patient and how to initiate the shock using the device 101. In an example, the electronic device 104 may be configured to implement the shock delivery program 157 and the artifact suppression program 159. For example, the electronic device 104 may perform an analysis of the ECG signal and determine a classification of the patient's heart rhythm to determine a shock/no-shock decision. For example, the electronic device 104 may determine the shock/no-shock decision based on the ECG signal during an interval when the patient is not being subject to CPR and/or without a reference signal (e.g., chest pressure, chest displacement, chest acceleration, compression depth, or thoracic impedance) that is measured concurrently (e.g., accelerometers or other sensors) with the ECG signal. The electronic device 104 may filter the received ECG signal of the patient to suppress CPR-related artifacts, caused by CPR being conducted on the patient, to enable the electronic device 104 to perform the shock/no-shock decision determinations even when a patient may be undergoing CPR. In an example, the electronic device 104 may output the filtered ECG signal to the device 101 for the device 101 to analyze the filtered ECG signal and perform the shock/no-shock decision determination. As a further example, the electronic device 104 may perform the shock/no-shock decision determination and output an alert to the device 101 for the device 101 to signal (e.g., an audible and/or visual signal) to the operator that a shock of the patient is necessary. As a further example, the electronic device 104 may display the alert or generate an audible alert to the operator to signal to the operator that a shock is necessary.

For example, the server 106 may include a group of one or more servers. For example, all or some of the operations executed by the device 101 may be executed in a different one or a plurality of electronic devices (e.g., the device 101, the electronic device 104, and/or the server 106). According to one example embodiment, if the device 101 needs to perform a certain function or service either automatically or based on a request, the device 101 may request at least some parts of functions related thereto alternatively or additionally to a different electronic device (e.g., the electronic device 104 and/or the server 106) instead of executing the function or the service autonomously. The different electronic devices (e.g., the electronic device 104, or the server 106) may execute the requested function or additional function, and may deliver a result thereof to the device 101. The device 101 may provide the requested function or service either directly or by additionally processing the received result. For example, a cloud computing, distributed computing, or client-server computing technique may be used. As an example, the device 101 may communicate with the electronic device 104 to provide the electronic device 104 the ECG signal information for the patient. The electronic device 104 may be configured to process the ECG signal to suppress the CPR-related artifacts and provide the filtered ECG signal to the device 101, wherein the device 101 may perform the shock/no-shock decision determination based on the filtered ECG signal received from the electronic device 104. As a further example, the electronic device 104 may perform the shock/no-shock decision determination and provide an alert to the device 101 to cause the device 101 to signal to the operator a shock of the patient is necessary. As a further example, the electronic device 104 may display the alert or audibly indicate the alert to the operator that a shock is necessary. As a further example, the device 101 may provide ECG signals of the patient to the server 106, wherein the server 106 may store the ECG signals, including the filtered signal with the suppressed CPR-related artifacts and the unfiltered signal with the CPR-related artifacts for further processing.

Figure 2:
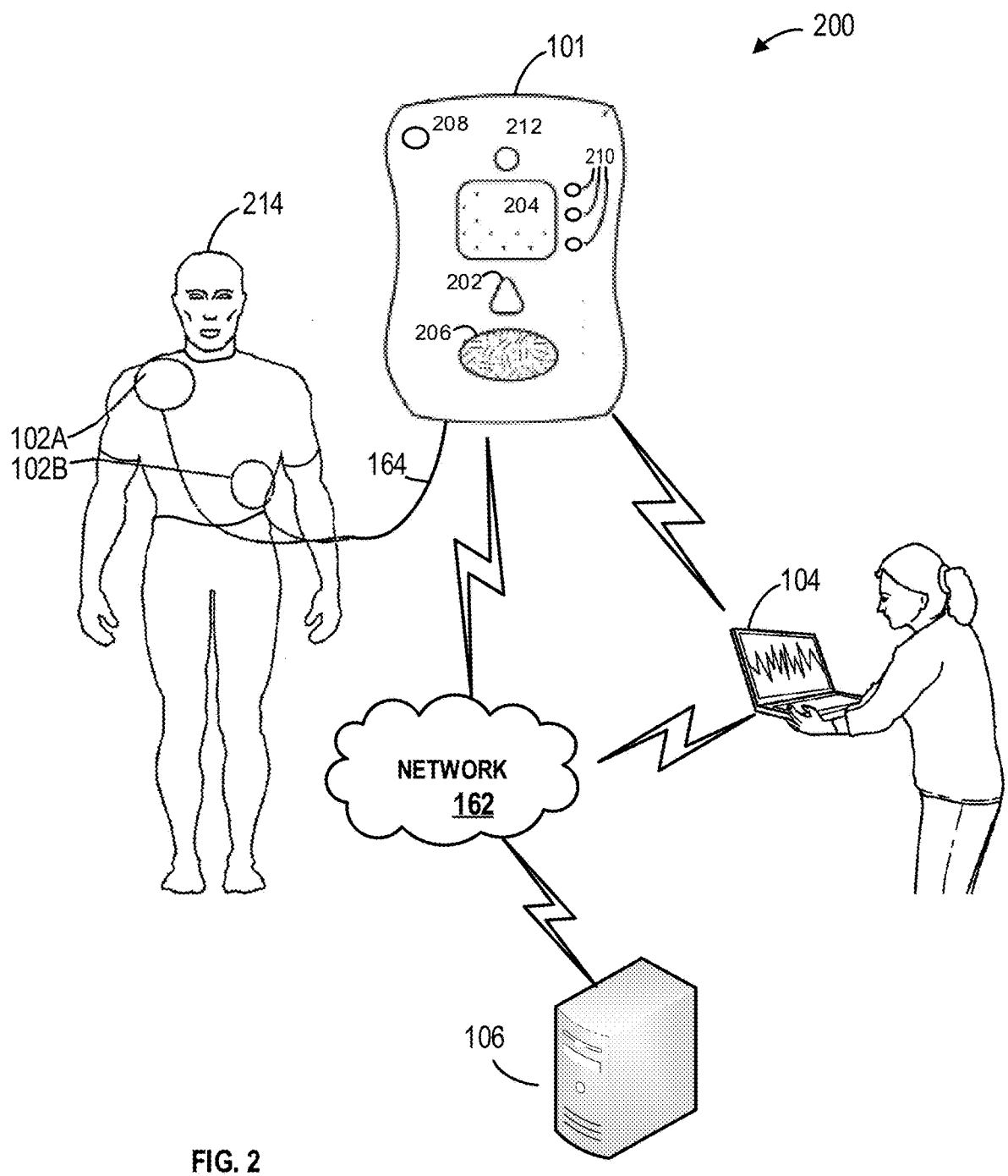
FIG. 2 shows another example system environment.
Figure 3A:
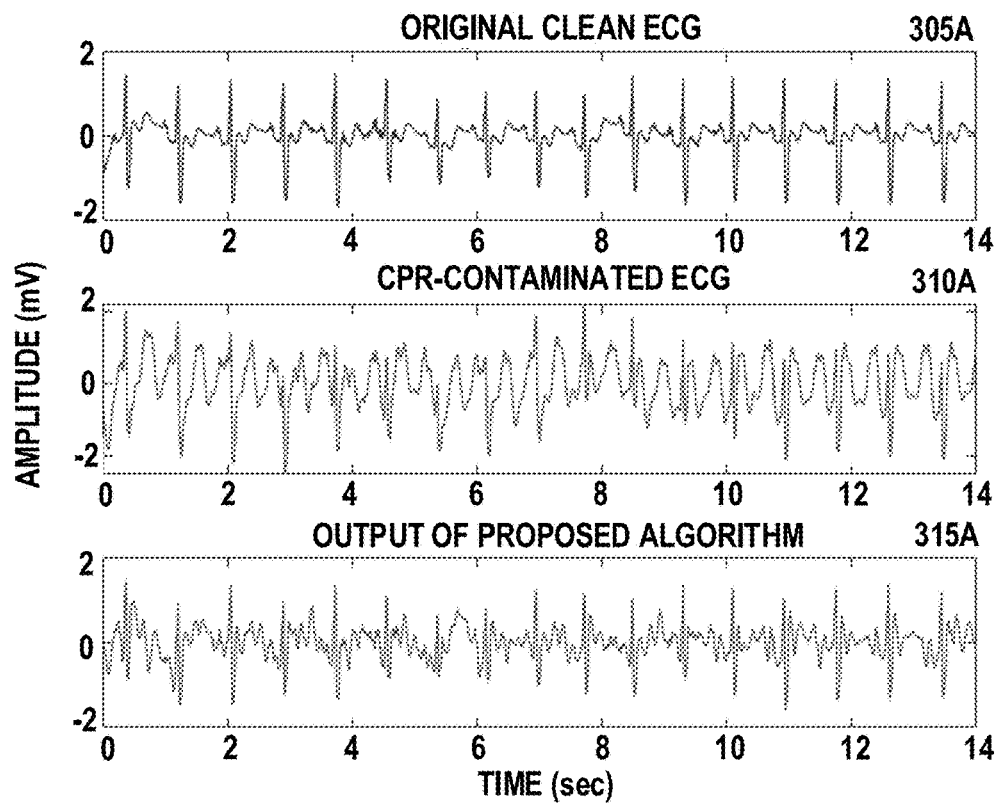
FIGS. 3A-3H show example ECG signal data.
Figure 3B:
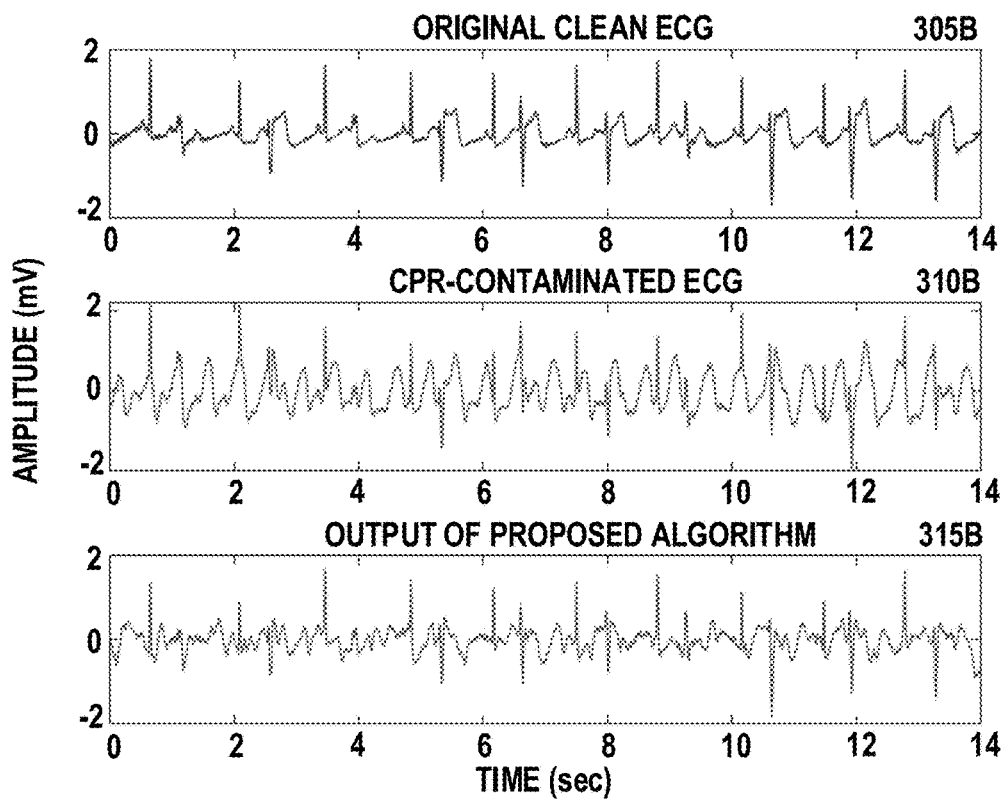
Figure 3C:
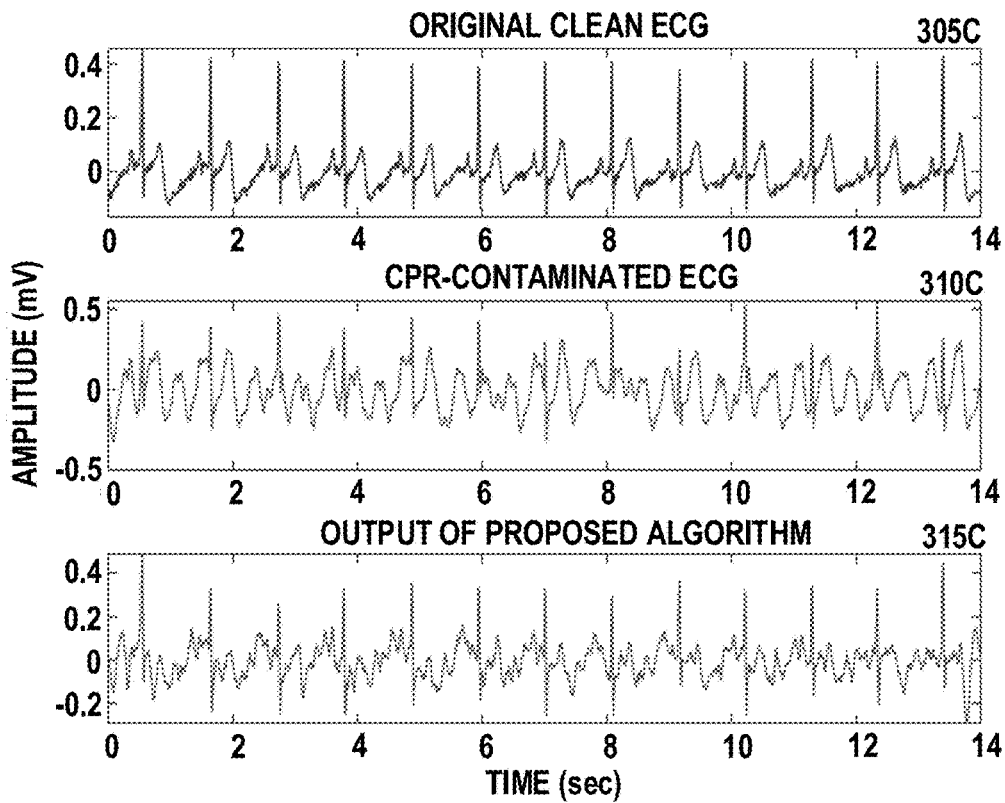
Figure 3D:
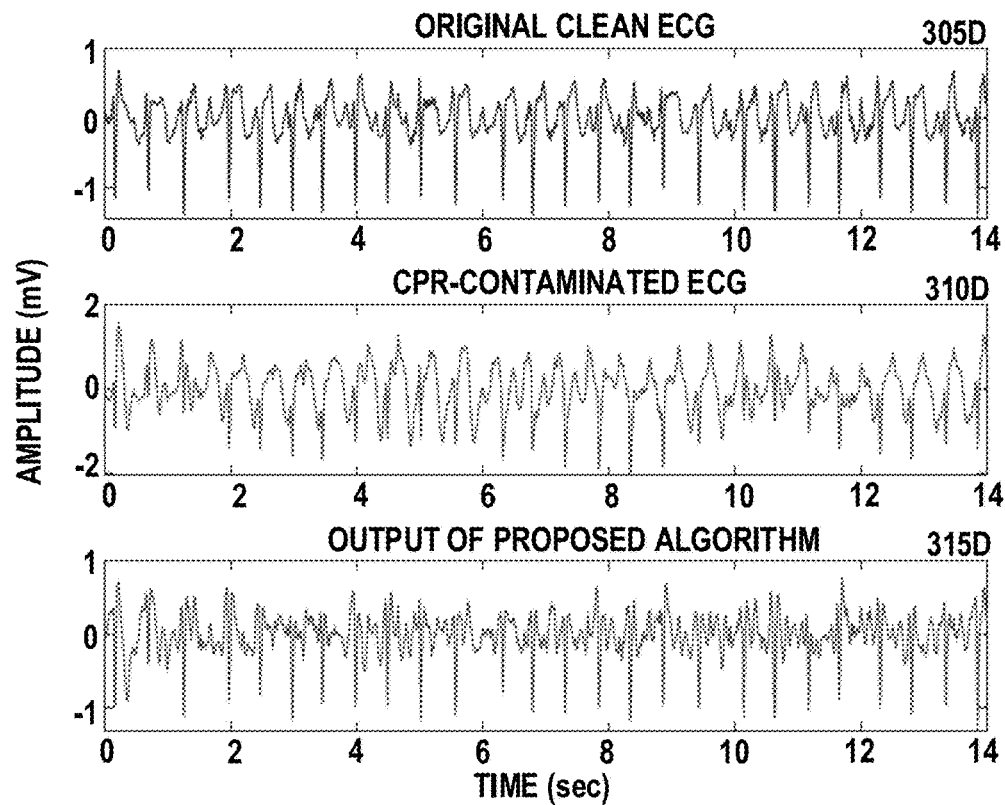
Figure 3E:
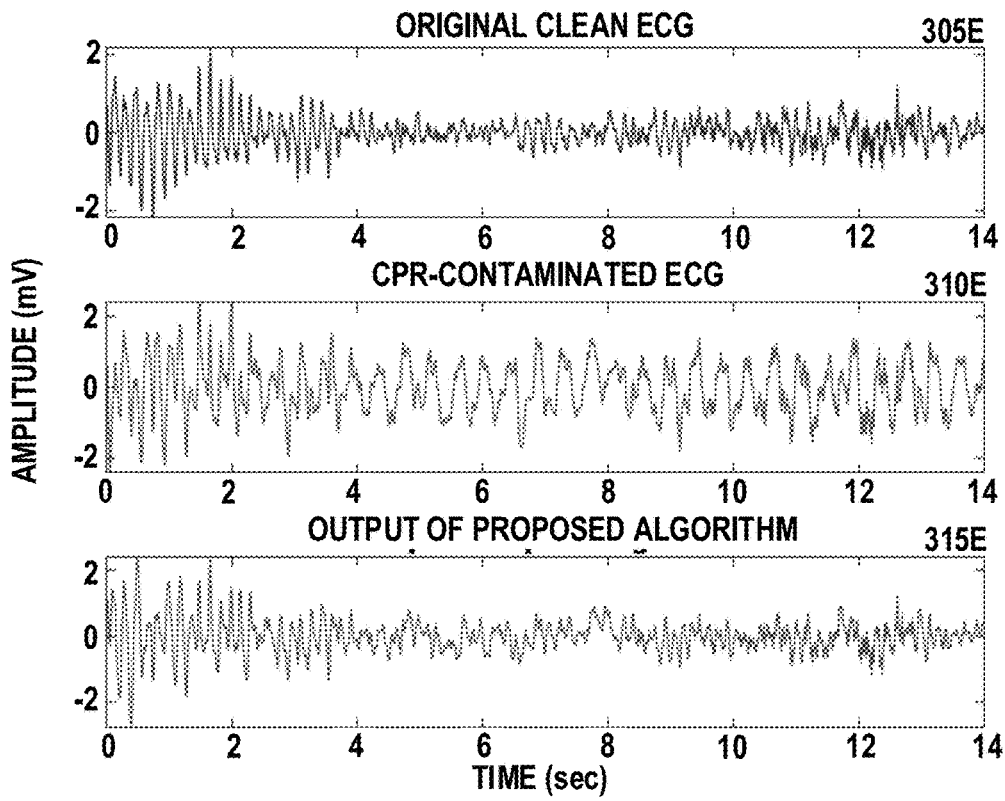
Figure 3F:
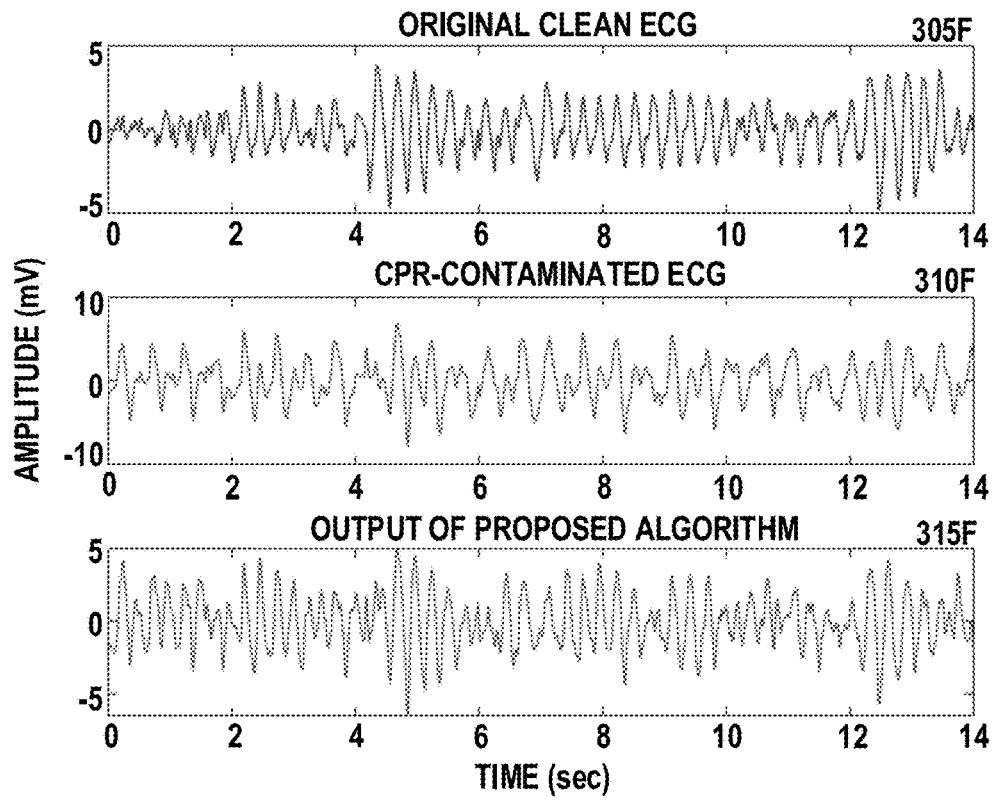
Figure 3G:
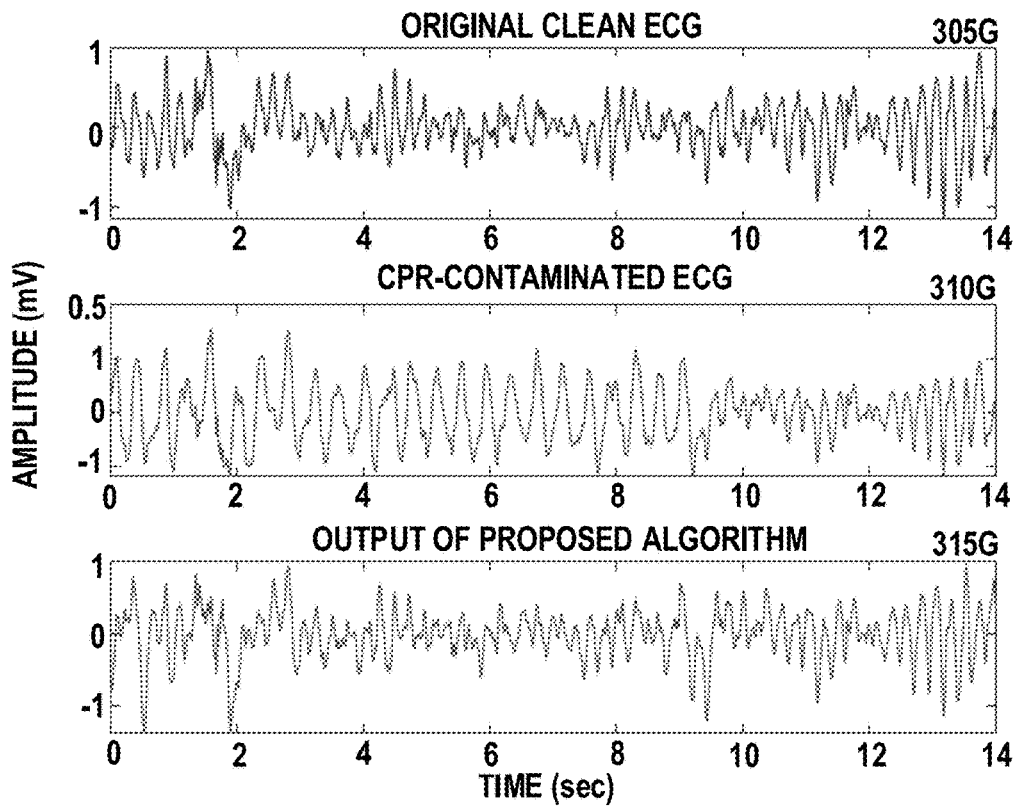
Figure 3H:
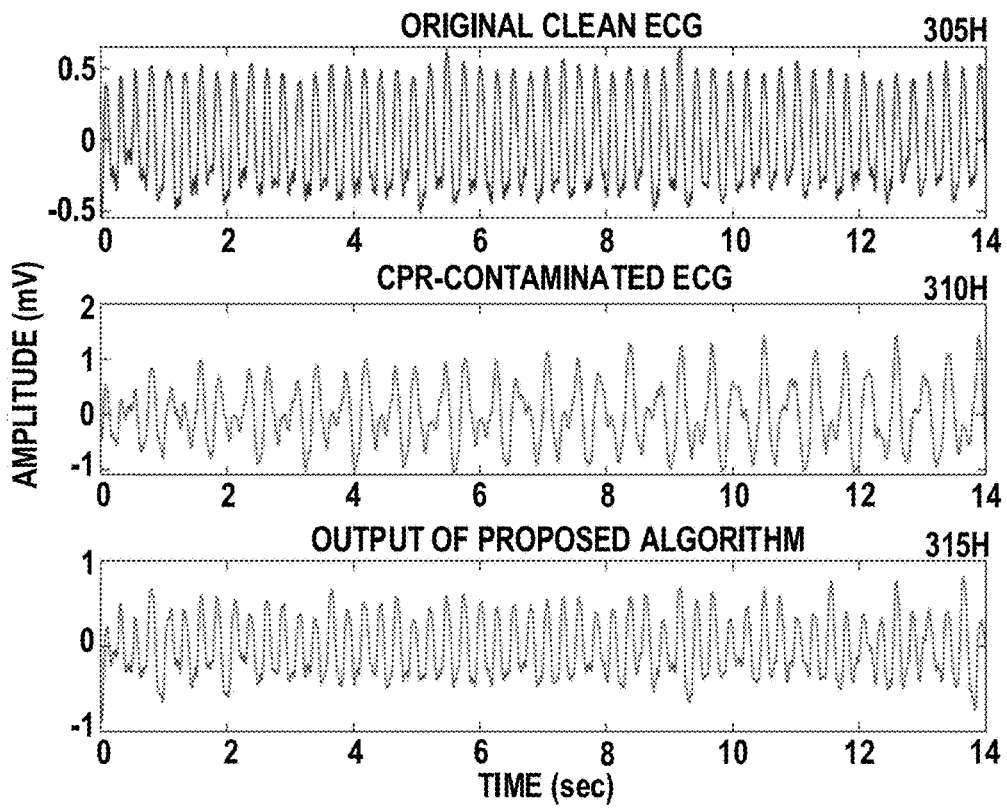

FIG. 2 shows an example system 200. The system 200 may comprise the device 101, the electronic device 104, the server 106, and the patient 214. The device 101 may comprise a defibrillator (e.g., automated external defibrillator (AED)) configured to perform a shock/no-shock decision determination with respect to the patient 214. For example, the device 101 may receive an ECG signal for the patient 214 based on sensors 102A-102B affixed to one or locations on the patient's body. The device 101 may perform a condition-based filtering process of the ECG signal for the patient 214 to suppress and/or remove CPR-related artifacts from the signal. The device 101 may analyze the filtered ECG signal to perform a shock/no-shock decision determination regardless of whether or not CPR is being performed on the patient 214.

The device 101 may comprise a shock delivery actuator 202, a display 204, a speaker 206, a status indicator 208, user interface buttons 210, and an on/off button/switch 212. The device 101 may be in communication with sensors 102A-102B via a wired communication interface 164 (e.g., leads). In an example, the sensors 102A-102B may be configured to function as defibrillation (e.g., therapeutic) shock pads that may be affixed to one or more location on the patient 214. The sensors 102A-102B may be configured to deliver a defibrillating, or other therapeutic, shock to the chest or other portion of a patient 214 via the communication interface 164 (e.g., leads). The sensors 102A-102B may be configured to receive the ECG signals associated with the patient 214. For example, the sensors 102A-102B may sense electrical activity within the patient's 214 chest and perform noise reduction and voltage/current normalization to the sensed electrical activity to determine an ECG signal for the patient 214 indicative of the electrical activity of the patient's heart. In an example, if the patient 214 is undergoing CPR, the ECG signal for the patient 214 may further include CPR-related artifacts.

The device 101 may analyze the ECG signal for the patient 214 to perform the shock/no-shock decision determination regarding the patient 214. If a shock is determined to be necessary, the device 101 may cause the speaker 206 and/or the display 204 to output audio and/or visual instructions to the operator on how to apply the sensors 102A-102B to the patient 214 and how to initiate a shock using the shock delivery actuator 202. Once the sensors 102A-102B have been applied to the patient 214 and the device 101 has determined a shock is necessary, the shock delivery actuator 202 may be pressed or actuated, sending an electrical charge from a battery of the device 101 through the sensors 102A-102B (e.g., defibrillation pads) to the patient 214. In an example, the device 101 may automatically deliver the therapeutic shock to the patient 214 based on determining that a shock is necessary, after an alert is output to the operator for a predetermined time interval, notifying the operator that a shock is necessary and will be performed on the patient 214 after the predetermined time interval.

In an example, as shown in FIG. 2, an operator may interact with an electronic device 104 configured to receive the ECG signals for the patient 214 from the device 101. The electronic device 104 may perform the shock/no-shock decision determination based on the ECG signal for the patient 214 received from the device 101. The electronic device 104 may be configured to display to an operator how to apply the pads (e.g., sensors 102A-102B) to the patient 214 and how to initiate the shock using the device 101. In an example, the electronic device 104 may be configured to implement the shock delivery program 157 and the artifact suppression program 159. For example, the electronic device 104 may perform an analysis of the ECG signal for the patient 214 and determine a classification of the patient's heart rhythm to determine a shock/no-shock decision. For example, the electronic device 104 may determine the shock/no-shock decision based on the ECG signal during an interval when the patient 214 is not receiving CPR and/or without a reference signal (e.g., chest pressure, chest displacement, chest acceleration, compression depth, or thoracic impedance) that is measured concurrently (e.g., accelerometers or other sensors) with the ECG signal while the patient 214 is receiving CPR. The electronic device 104 may filter the received ECG signal to suppress and/or remove CPR-related artifacts to enable the electronic device 104 to perform the shock/no-shock decision determinations even when a patient may be undergoing CPR. In an example, the electronic device 104 may output the filtered ECG signal to the device 101 for the device 101 to analyze the filtered ECG signal and perform the shock/no-shock decision determination. As a further example, the electronic device 104 may perform the shock/no-shock decision determination and output an alert to the device 101 for the device 101 to signal to the operator that a shock or the patient 214 is necessary. As a further example, the electronic device 104 may display or audibly indicate the alert to the operator to signal to the operator that a shock is necessary.

In an example, the device 101 may output the ECG signal of the patient 214 to the server 106, wherein the server 106 may store the ECG signals, including the filtered signal with the suppressed CPR-related artifacts and the unfiltered signal with the CPR-related artifacts for further processing. As a further example, the electronic device 104 may output the ECG signal data of the patient 214 to the server 106. The server 106 may be configured to store ECG signal data for each patient from which it was received.

FIGS. 3A-3H show charts comprising examples of ECG signal data 305A-305H, ECG signal data with CPR-related artifacts 310A-310H, and filtered ECG signal data with the CPR-related artifacts suppressed from the data 315A-315H. FIGS. 3A-3D show the performance of the condition-based filter on four different representative non-shockable ECG rhythm types, wherein each panel of charts represents the ECG signal data segment of a different patient. FIGS. 3E-3H show the performance of the condition-based filter on four different representative shockable ECG rhythm types, wherein each panel of charts represents the ECG signal data segment of a different patient. As shown in FIGS. 3A-3H, the condition-based algorithm removes a significant portion of the CPR-related artifacts from the ECG signal. Depending on the type of rhythm, the method is designed to filter only the CPR artifacts without removing the dynamics of interest.

Figure 4A:
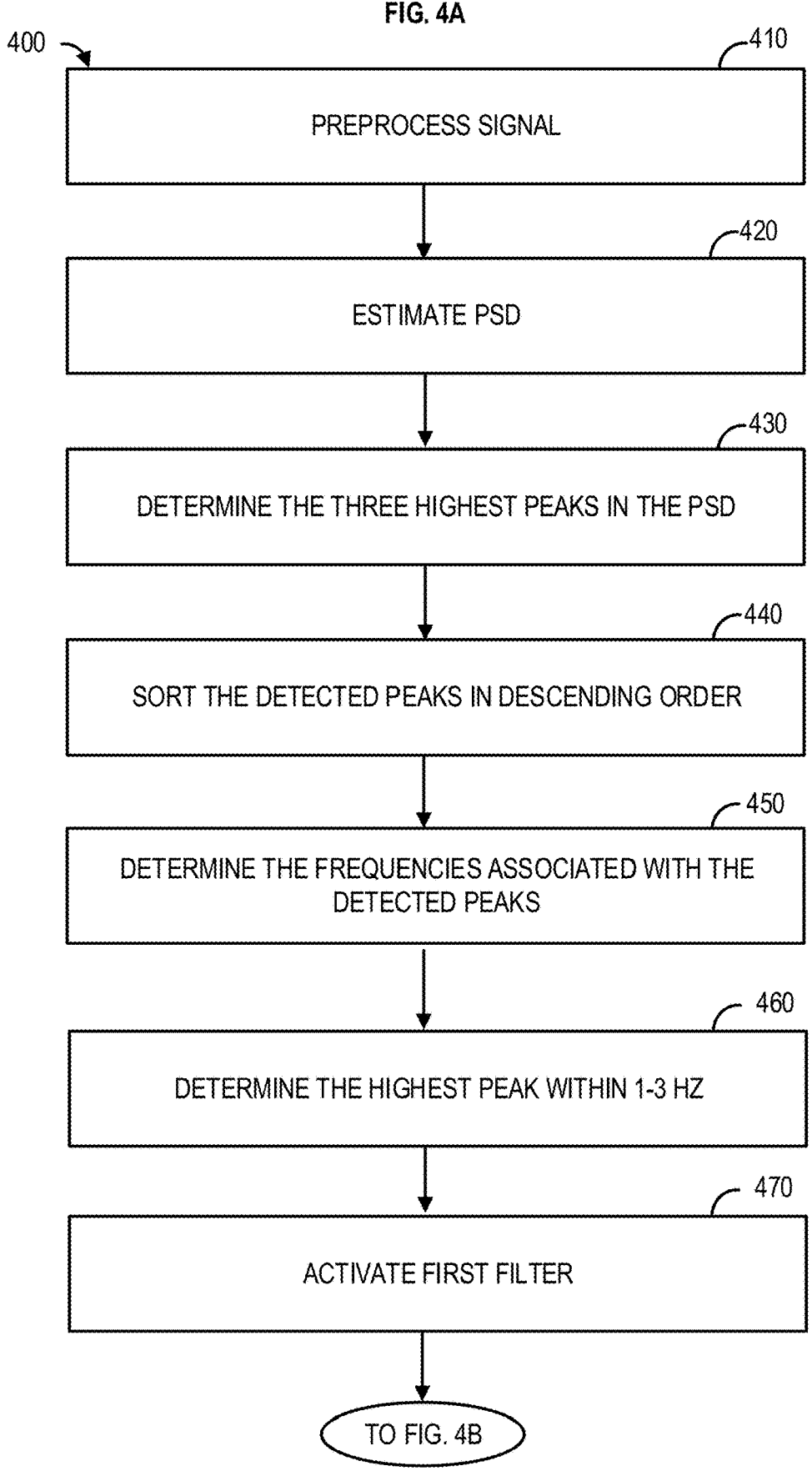

FIGS. 4A-4B show a flowchart of an example method 400 for condition-based artifact suppression of an ECG signal. The method 400 may be implemented in whole or in part, by one or more of the device 101, the electronic device 104, the sever 106, or any other suitable computing device. The ECG signal may be converted into a time series, wherein the artifact suppression method may be performed on the ECG signal time series. The condition-based filtering method may comprise one, two, or three stop-band filters. The status of each stop-band filter may be set to active or non-active depending on the result of a defined condition. The cut-off frequencies for the stop-band filters may be updated according to the characteristics of the ECG signal time series segment. Non-shockable ECG signal samples may have a spectral power in the higher frequency bands (e.g., above 10 Hz) whereas the shockable ECG signal samples do not share this characteristic. After suppressing the frequency of the largest spectral peak of the CPR-related artifact for non-shockable ECG signal data, the total power within the 10-15 Hz range is determined. The total power is then used to determine whether or not a second filter is needed to remove the second largest spectral peak.

At 410, the heart rate time series (e.g., ECG signal) may be preprocessed by applying a notch filter. For example, the notch filter may comprise a second order infinite impulse response (IIR) notch filter. The notch filter may be configured to remove 60 Hz electrical noise from the raw ECG signal received from the sensors 102A-102B. A wavelet implementation plus averaging may also be applied to the ECG signal to remove glitches and to achieve a smoother signal. The reconstructed approximation signal may then be subsequently subtracted from the original signal.

At 420, a power spectral density (PSD) for the ECG signal is estimated using Welch's overlapped segment averaging spectral estimator. For example, the modified periodograms may be averaged using the Hamming window to obtain the PSD estimate.

At 430, the three highest peaks in the PSD of the CPR-contaminated ECG signal may be determined. For example, the three highest peaks may be determined for a period of time of the ECG signal. The period of time may be a preset period of time. At 440, the three highest peaks of the PSD of the ECG signal may be sorted in descending order (e.g., Peak 1, Peak 2, and Peak 3). At 450, the frequencies (e.g., F1, F2, and F3) associated with each of the corresponding detected peaks (e.g., Peak 1, Peak 2, and Peak 3) in the PSD of the ECG signal are determined. In 460, a first frequency (F1) may be determined to be the frequency of the frequency peaks between the frequencies of 1-3 Hz. For example, the fundamental frequency of the chest compressions that occur while a patient is receiving CPR is localized within the 1-3 Hz frequency range.

At 470, a first stop-band filter is turned on, or activated, and applied to the ECG signal to generate a filtered ECG signal. For example, the cutoff frequency of the first stop-band filter comprises the first frequency (F1) of Peak 1 (e.g., the highest peak of the three highest peaks of the PSD of the ECG signal). At 480, a determination is made of the spectral power in the 10-15 Hz frequency band of the filtered ECG signal.

At 490, a determination is made as to whether any of the remaining frequency peaks (e.g., the two highest remaining peaks of the PSD of the ECG signal, Peak 2 and Peak 3) are divisible by the first frequency associated with Peak 1 (the highest peak of the PSD of the ECG signal). For example, if any of the remaining frequency peaks is divisible by the first frequency, the YES branch may be followed to 492. At 492, a second frequency may be determined. For example, the second frequency may be determined as comprising or being the frequency of the remaining frequency peaks that is determined to be divisible by the first frequency. If, for example, both frequency peaks are determined to be divisible by the first frequency, the second frequency may comprise the frequency of the remaining frequency peaks of the PSD with the highest peak. At 493, the second frequency may be evaluated to determine if the second frequency is not within 3-6 HZ and/or the spectral power may be evaluated to determine if the spectral power that is in the 10-15 Hz frequency band satisfies a threshold value. For example, the threshold value may be a preset value. For example, the threshold value may comprise or be set at 0.07 Watt/Hz in order to avoid filtering the artifacts' second highest spectral peak from shockable rhythms. Spectral distortion may be introduced to the filtered ECG signal associated with shockable heart rhythms if the artifacts' second highest spectral peak is removed because the fundamental frequency component of the shockable rhythms overlap with the harmonic frequencies of the chest compressions while the patient is receiving CPR. The upper limit of the spectral power in the 10-15 Hz frequency band for the filtered ECG signal associated with shockable heart rhythms is 0.072. Therefore, 0.07 Watt/Hz may be set to avoid filtering the artifacts' second highest spectral peak from the filtered ECG signal associated with shockable heart rhythms. Based on a determination that the second frequency is not within 3-6 Hz or that the spectral power that is within 10-15 Hz satisfies a threshold value, then the YES branch may be followed to 494. At 494, the second stop-band filter may be turned on, or activated, and applied to the filtered ECG signal. For example, the cutoff frequency of the second stop-band filter may comprise or be the value of the second frequency. The filtered signal (e.g., the modified ECG signal) according to the second stop-band filter may then be analyzed in order to determine the shock/no-shock decision. Returning, to 493, based on a determination that the second frequency is within 3-6 Hz and that the spectral power that is within 10-15 Hz does not satisfy a threshold value, then the NO branch may be followed to 497. At 497, the first stop-band filter remains active and the filtered ECG signal according to the first stop-band filter may be used to determine the shock/no-shock decision.

Returning to 490, if none of the frequencies of the remaining frequency peaks is divisible by the first frequency, the NO branch is followed to 495. At 495, the first frequency may be evaluated to determine if the first frequency is less than 1.5 Hz and/or the spectral power may be evaluated to determine if the spectral power in the 10-15 Hz frequency band satisfies a threshold value. For example, the threshold value may be a preset value. For example, the threshold value may comprise or be set at 0.07 Watt/Hz in order to avoid filtering the CPR artifacts' second highest spectral peak from shockable rhythms. Spectral distortion may be introduced to the filtered ECG signal associated with shockable heart rhythms if the artifacts' second highest spectral peak is removed because the fundamental frequency component of the shockable rhythms overlap with the harmonic frequencies of the chest compressions while the patient is receiving CPR. The upper limit of the spectral power in the 10-15 Hz frequency band for the filtered ECG signal associated with shockable heart rhythms is 0.072. Therefore 0.07 Watt/Hz may be set to avoid filtering the artifacts' second highest spectral peak from the filtered ECG signal associated with shockable heart rhythms. Based on a determination that the first frequency is less than 1.5 Hz or that the spectral power in the 10-15 Hz frequency band satisfies a threshold value, then the YES branch may be followed to 496.

At 496, a third stop-band filter is turned on, or activated, and applied to the filtered ECG signal. For example, the cutoff frequency for the third stop-band filter may comprise or be two times the first frequency. The filtered signal according to the third stop-band filter (e.g., the modified ECG signal) may then be used to determine the shock/no-shock decision for the device 101. Returning, to 495, based on a determination that the first frequency is greater than 1.5 Hz and that the spectral power in the 10-15 Hz frequency band does not satisfy a threshold value, then the NO branch may be followed to 497. At 497, the first stop-band filter remains active and the filtered ECG signal according to the first stop-band filter is then used to determine the shock/no-shock decision.

Figure 5:
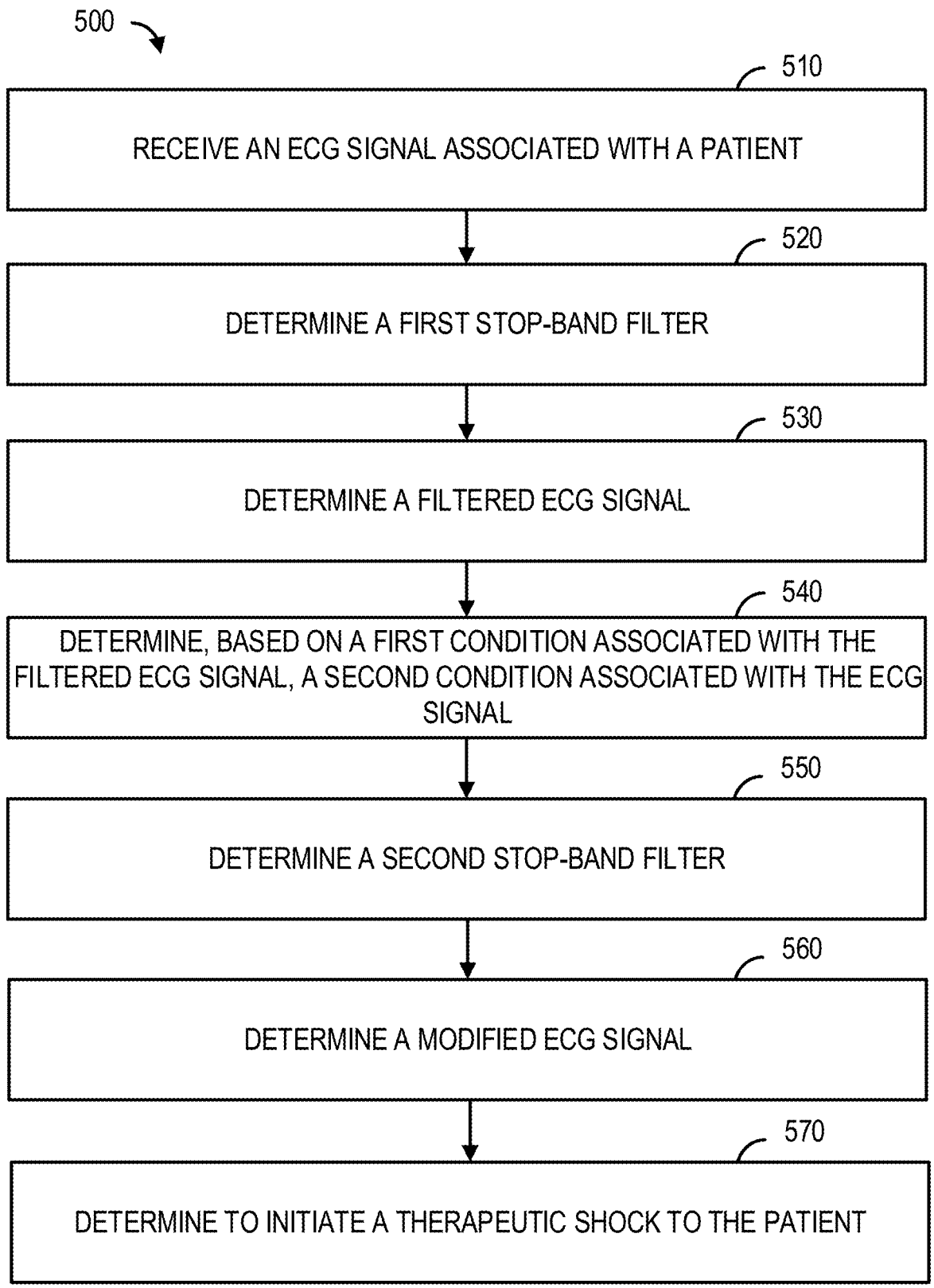
FIG. 5 shows a flowchart of an example method.

FIG. 5 shows a flowchart of an example method 500. The method 500 may be implemented in whole or in part, by one or more of, the device 101, the electronic device 104, the sever 106, or any other suitable device. At step 510, an ECG signal associated with a patient may be received. The ECG signal may comprise one or more artifacts associated with cardiopulmonary resuscitation (CPR) or other life-saving actions being performed on the patient. The ECG signal may be received from one or more defibrillation pads affixed to one or more locations of the patient.

At step 520, a first stop-band filter may be determined. For example, the first stop-band filter may be determined based on the power spectral density (PSD) of the ECG signal. The frequencies of the three highest peaks of the PSD may be determined. The cutoff frequency (e.g., first frequency) of the first stop-band filter may comprise the frequency of the three determined frequencies that is within the 1-3 Hz frequency range. At step 530, a filtered ECG signal may be determined based on applying the first stop-band filter to the ECG signal.

At step 540, a second condition associated with the filtered ECG signal may be determined based on a first condition associated with the filtered ECG signal. For example, the first condition associated with the filtered ECG signal may be determined based on processing the filtered ECG signal. For example, the first condition may comprise whether any of the frequencies of the remaining frequency peaks, determined from the PSD, are divisible by the cutoff frequency of the first stop-band filter. A second frequency may be determined based on whether any of the frequencies of the remaining frequency peaks, determined from the PSD, are divisible by the cutoff frequency of the first stop-band filter. In addition, a spectral power in the 10-15 Hz frequency band of the filtered ECG signal may be determined. If at least one of the frequencies of the remaining frequency peaks is divisible by the cutoff frequency of the first stop-band filter, the second frequency may comprise the frequency that is divisible by the cutoff frequency, for example, and the second condition may comprise whether the second frequency is outside of the 3-6 HZ frequency range or whether the spectral power in the 10-15 Hz frequency band satisfies a threshold value. If none of the frequencies of the remaining frequency peaks is divisible by the cutoff frequency of the first stop-band filter, then the second condition may comprise whether the spectral power in the 10-15 Hz frequency band satisfies the threshold value or whether the first frequency is less than 1.5 Hz.

At step 550, the second stop-band filter may be determined based on satisfying the second condition. As an example, a cutoff frequency of the second stop-band filter may be determined based on the second frequency being outside of the 3-6 Hz frequency range or the spectral power in the 10-15 Hz frequency band satisfying the threshold value (e.g., second condition being satisfied), wherein the cutoff frequency of the second stop-band filter may comprise the second frequency. As a further example, the cutoff frequency of the second stop-band filter may be determined based on the spectral power in the 10-15 Hz frequency band satisfying the threshold value or the first frequency being less than 1.5 Hz (e.g., second condition being satisfied), wherein the cutoff frequency of the second stop-band filter may comprise two times the cutoff frequency of the first stop-band filter.

At step 560, a modified ECG signal may be generated based on an application of the second stop-band filter to the filtered ECG signal. The modified signal may comprise an attenuated ECG signal wherein the artifact signal may be suppressed according to the application of the second stop-band filter to the filtered ECG signal.

At step 570, a determination of whether to initiate a therapeutic shock to the patient may be made based on the modified ECG signal. For example, an alert may be generated based on analyzing the modified ECG signal. For example, the modified ECG signal may be analyzed to determine a classification of the patient's heart rhythm, wherein the alert may be generated based on the classification of the patient's heart rhythm. The classification may be indicative of a shockable heart rhythm associated with the modified ECG signal. In an example, the alert may comprise a notification to stand clear of the patient for a therapeutic shock to be delivered to the patient. The therapeutic shock may be delivered through pads (e.g., sensors 102A-102B) affixed to one or more locations of the patient's body. As an example, the therapeutic shock may be implemented automatically based on the alert. As a further example, the alert may be output to a display for the operator to cause the device (e.g., device 101) to deliver the therapeutic shock to the patient via the pads (e.g., sensors 102A-102B) affixed to the one or more locations of the patient's body.

Figure 6:
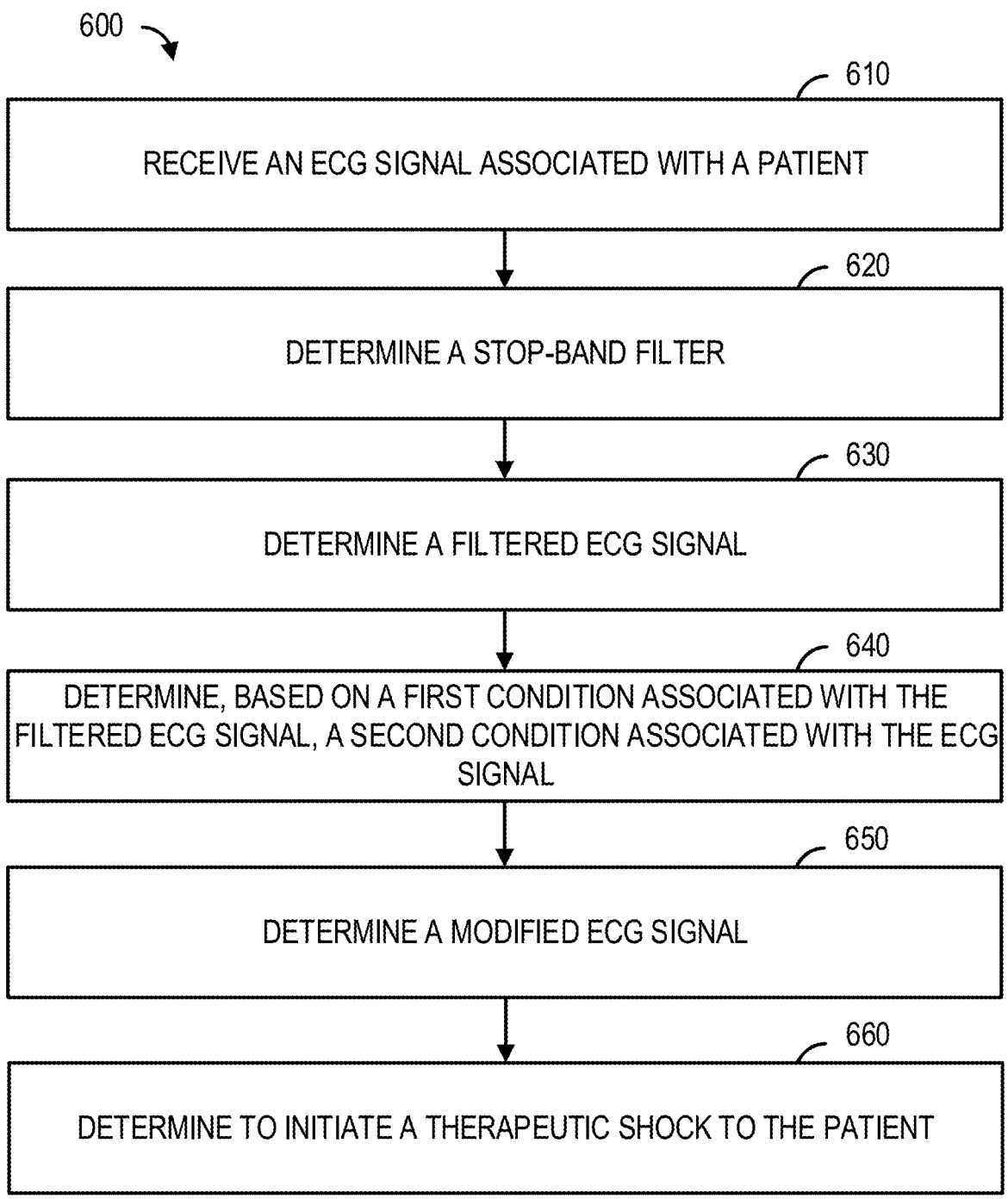
FIG. 6 shows a flowchart of an example method.

FIG. 6 shows a flowchart of an example method 600. The method 600 may be implemented in whole or in part, by one or more of, the device 101, the electronic device 104, the sever 106, or any other suitable device. At step 610, an ECG signal associated with a patient is received. The ECG signal may comprise one or more artifacts associated with cardiopulmonary resuscitation (CPR) or other life-saving actions being performed on the patient. The ECG signal may be received from one or more defibrillation pads affixed to one or more locations of the patient.

At step 620, a stop-band filter may be determined. For example, the stop-band filter may be determined based on the power spectral density (PSD) of the ECG signal. The frequencies of the three highest peaks of the PSD may be determined. The cutoff frequency (e.g., first frequency) of the stop-band filter may comprise the frequency of the three determined frequencies that is within the 1-3 Hz frequency range. At step 630, a filtered ECG signal is determined based on an application of the stop-band filter to the ECG signal.

At step 640, a second condition associated with the filtered ECG signal may be determined based on a first condition associated with the filtered ECG signal. For example, the first condition associated with the filtered ECG signal may be determined based on processing the filtered ECG signal. For example, the first condition may comprise whether any of the frequencies of the remaining frequency peaks, determined from the PSD, are divisible by the cutoff frequency of the stop-band filter. A second frequency may be determined based on whether any of the frequencies of the remaining frequency peaks, determined from the PSD, are divisible by the cutoff frequency of the stop-band filter. In addition, a spectral power in the 10-15 Hz frequency band of the filtered ECG signal may be determined. If at least one of the frequencies of the remaining frequency peaks is divisible by the cutoff frequency of the stop-band filter, the second frequency may comprise the frequency that is divisible by the cutoff frequency, for example, and the second condition may comprise whether the second frequency is outside of the 3-6 HZ frequency range or whether the spectral power in the 10-15 Hz frequency band satisfies a threshold value. If none of the frequencies of the remaining frequency peaks are divisible by the cutoff frequency of the stop-band filter, then the second condition may comprise whether the spectral power in the 10-15 Hz frequency band satisfies the threshold value or whether the first frequency is less than 1.5 Hz.

At step 650, a modified ECG signal may be determined based on the second condition not being satisfied. As an example, if the second frequency is within the 3-6 HZ frequency range or the spectral power in the 10-15 Hz frequency band does not satisfy the threshold value, the modified ECG signal is determined to comprise the filtered ECG signal. As a further example, if the spectral power in the 10-15 Hz frequency band does not satisfy the threshold value or the first frequency is greater than 1.5 Hz, similarly, the modified ECG signal is determined to comprise the filtered ECG signal. The modified ECG signal may comprise an attenuated ECG signal, wherein the artifact signal may be suppressed according to the application of the stop-band filter to the filtered ECG signal.

At step 660, a determination of whether to initiate a therapeutic shock to the patient may be made based on the modified ECG signal. For example, an alert may be generated based on analyzing the modified ECG signal. For example, the modified ECG signal may be analyzed to determine a classification of the patient's heart rhythm, wherein the alert may be generated based on the classification of the patient's heart rhythm. The classification may be indicative of a shockable heart rhythm associated with the modified ECG signal. In an example, the alert may comprise a notification to stand clear of the patient for a therapeutic shock to be delivered to the patient. The therapeutic shock may be delivered through pads (e.g., sensors 102A-102B) affixed to one or more locations of the patient's body. As an example, the therapeutic shock may be implemented automatically based on the alert. As a further example, the alert may be output to a display for the operator to cause the device (e.g., device 101) to deliver the shock to the patient via the pads (e.g., sensors 102A-102B) affixed to the one or more locations of the patient's body.

Figure 7:
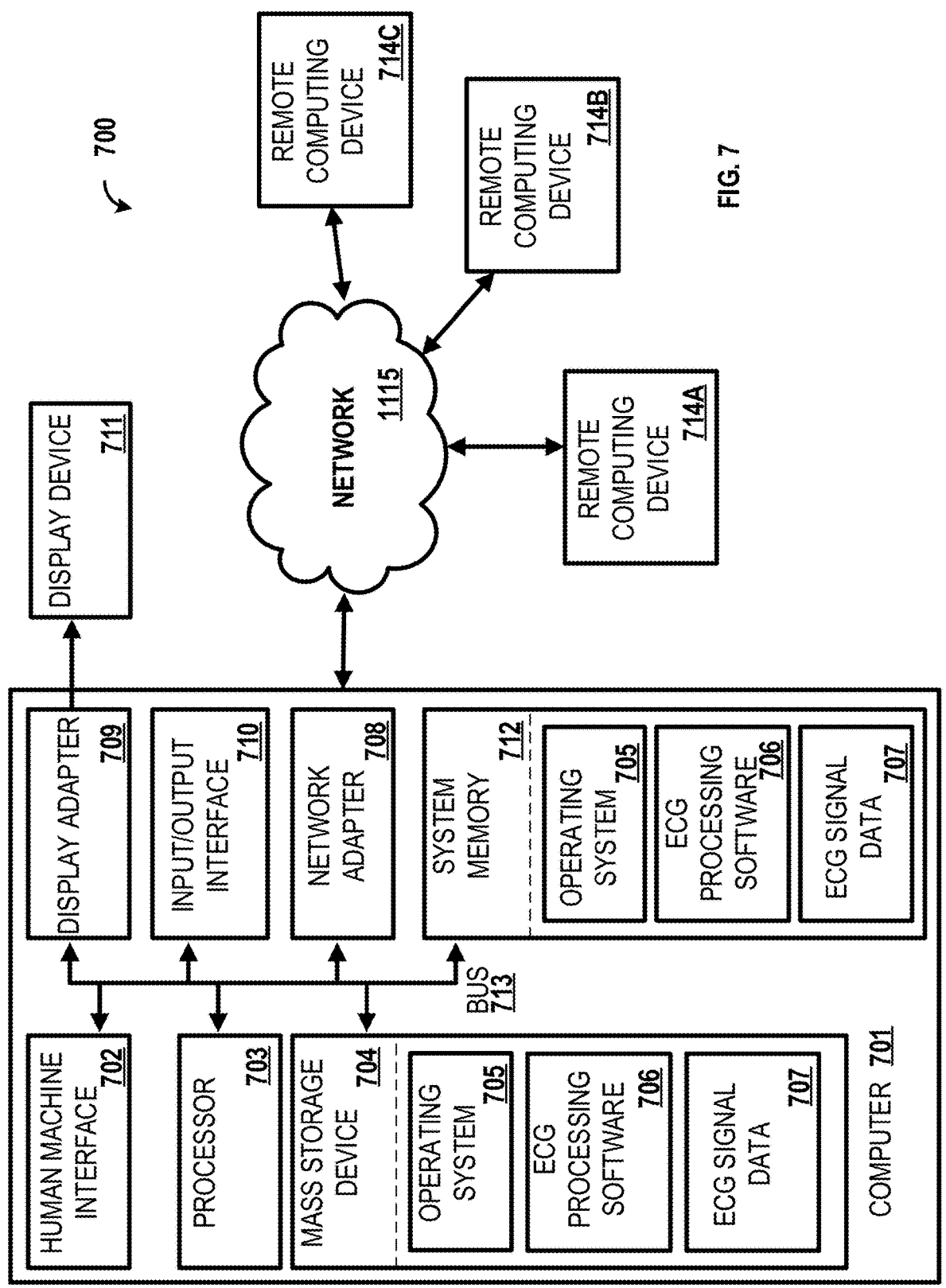
FIG. 7 shows a block diagram of a computing device for implementing the example methods.

In an example, the methods and systems may be implemented on a computer 701 as shown in FIG. 1 and described below. By way of example, device 101 and electronic device 104 of FIG. 1 may be a computer 701 as shown in FIG. 7. Similarly, the methods and systems disclosed can utilize one or more computers to perform one or more functions in one or more locations. FIG. 7 shows a block diagram of an example operating environment 700 for performing the disclosed methods. For example, operating environment 700 is only an example of an operating environment and is not intended to suggest any limitation as to the scope of use or functionality of operating environment architecture. Neither should the operating environment 700 be interpreted as having any dependency or requirement relating to any one or combination of components illustrated in the example operating environment 700.

The present methods and systems can be operational with numerous other general purpose or special purpose computing system environments or configurations. Examples of well-known computing systems, environments, and/or configurations that can be suitable for use with the systems and methods comprise, but are not limited to, personal computers, server computers, laptop devices, and multiprocessor systems. Additional examples comprise set top boxes, programmable consumer electronics, network PCs, minicomputers, mainframe computers, distributed computing environments that comprise any of the above systems or devices, and the like.

The processing of the disclosed methods and systems can be performed by software components. The disclosed systems and methods can be described in the general context of computer-executable instructions, such as program modules, being executed by one or more computers or other devices. Generally, program modules comprise computer code, routines, programs, objects, components, data structures, and/or the like that perform particular tasks or implement particular abstract data types. The disclosed methods can also be practiced in grid-based and distributed computing environments where tasks are performed by remote processing devices that are linked through a communications network. In a distributed computing environment, program modules can be located in local and/or remote computer storage media such as memory storage devices.

Further, one skilled in the art will appreciate that the systems and methods disclosed herein can be implemented via a general-purpose computing device in the form of a computer 701. The computer 701 can comprise one or more components, such as one or more processors 703, a system memory 712, and a bus 713 that couples various components of the computer 701 comprising the one or more processors 703 to the system memory 712. In the case of multiple processors 703, the computer 701 may utilize parallel computing.

The bus 713 may comprise one or more of several possible types of bus structures, such as a memory bus, memory controller, a peripheral bus, an accelerated graphics port, or local bus using any of a variety of bus architectures. By way of example, such architectures can comprise an Industry Standard Architecture (ISA) bus, a Micro Channel Architecture (MCA) bus, an Enhanced ISA (EISA) bus, a Video Electronics Standards Association (VESA) local bus, an Accelerated Graphics Port (AGP) bus, and a Peripheral Component Interconnects (PCI), a PCI-Express bus, a Personal Computer Memory Card Industry Association (PCMCIA), Universal Serial Bus (USB) and the like. The bus 713, and all buses specified in this description can also be implemented over a wired or wireless network connection and one or more of the components of the computer 701, such as the one or more processors 703, a mass storage device 704, an operating system 705, ECG processing software 706, ECG signal data 707, a network adapter 708, the system memory 712, an Input/Output Interface 710, a display adapter 709, a display device 711, and a human machine interface 702, can be contained within one or more remote computing devices 714A-714C at physically separate locations, connected through buses of this form, in effect implementing a fully distributed system.

The computer 701 may operate on and/or comprise a variety of computer-readable media (e.g., non-transitory). Computer-readable media may be any available media that is accessible by the computer 701 and comprises non-transitory, volatile, and/or non-volatile media, removable and non-removable media. The system memory 712 has computer-readable media in the form of volatile memory, such as random access memory (RAM), and/or non-volatile memory, such as read-only memory (ROM). The system memory 712 typically can comprise data such as the ECG signal data 707 and/or program modules such as the operating system 705 and the ECG processing software 706 that are accessible to and/or are operated on by the one or more processors 703.

The computer 701 may also comprise other removable/non-removable, volatile/non-volatile computer storage media. The mass storage device 704 may provide non-volatile storage of computer code, computer-readable instructions, data structures, program modules, and other data for the computer 701. The mass storage device 704 may be a hard disk, a removable magnetic disk, a removable optical disk, magnetic cassettes or other magnetic storage devices, flash memory cards, CD-ROM, digital versatile disks (DVD) or other optical storage, random access memories (RAM), read-only memories (ROM), electrically erasable programmable read-only memory (EEPROM), and the like.

Any number of program modules can be stored on the mass storage device 704, such as, by way of example, the operating system 705 and the ECG processing software 706. One or more of the operating system 705 and the ECG processing software 706 (or some combination thereof) can comprise elements of the programming and the ECG processing software 706. The ECG signal data 707 can also be stored on the mass storage device 704. The ECG signal data 707 can be stored in any of one or more databases known in the art. Examples of such databases comprise, DB2®, Microsoft® Access, Microsoft® SQL Server, Oracle®, mySQL, PostgreSQL, and the like. The databases can be centralized or distributed across multiple locations within the network 715.

A user may enter commands and information into the computer 701 via an input device (not shown). Such input devices may comprise, but are not limited to, a keyboard, pointing device (e.g., a computer mouse, remote control), a microphone, a joystick, a scanner, tactile input devices such as gloves, and other body coverings, motion sensor, and the like These and other input devices may be connected to the one or more processors 703 via a human-machine interface 702 that is coupled to the bus 713, but may be connected by other interface and bus structures, such as a parallel port, game port, an IEEE 1394 Port (also known as a Firewire port), a serial port, network adapter 708, and/or a universal serial bus (USB).

A display device 711 may also be connected to the bus 713 via an interface, such as a display adapter 709. It is contemplated that the computer 701 may have more than one display adapter 709 and the computer 701 may have more than one display device 711. A display device 711 may be a monitor, an LCD (Liquid Crystal Display), light-emitting diode (LED) display, television, smart lens, smart glass, and/or a projector. In addition to the display device 711, other output peripheral devices may comprise components such as speakers (not shown) and a printer (not shown) which may be connected to the computer 701 via Input/Output Interface 710. Any step and/or result of the methods may be output (or caused to be output) in any form to an output device. Such output may be any form of visual representation, including, but not limited to, textual, graphical, animation, audio, tactile, and the like. The display 711 and computer 701 may be part of one device, or separate devices.

The computer 701 can operate in a networked environment using logical connections to one or more remote computing devices 714A-714C. By way of example, a remote computing device 714A-714C can be a personal computer, computing station (e.g., workstation), portable computer (e.g., laptop, mobile phone, tablet device), smart device (e.g., smartphone, smart watch, activity tracker, smart apparel, smart accessory), security and/or monitoring device, a server, a router, a network computer, a peer device, edge device or other common network node, and so on. Logical connections between the computer 701 and a remote computing device 714A-714C can be made via a network 715, such as a local area network (LAN) and/or a general wide area network (WAN). Such network connections can be through the network adapter 708. The network adapter 708 can be implemented in both wired and wireless environments. Such networking environments are conventional and commonplace in dwellings, offices, enterprise-wide computer networks, intranets, and the Internet.

Application programs and other executable program components such as the operating system 705 are illustrated herein as discrete blocks, although it is recognized that such programs and components can reside at various times in different storage components of the computing device 701, and are executed by the one or more processors 703 of the computer 701. An implementation of the ECG processing software 706 can be stored on or transmitted across some form of computer readable media. Any of the disclosed methods can be performed by computer readable instructions embodied on computer readable media. Computer readable media can be any available media that can be accessed by a computer. By way of example and not meant to be limiting, computer readable media can comprise "computer storage media" and "communications media." "Computer storage media" can comprise volatile and non-volatile, removable and non-removable media implemented in any methods or technology for storage of information such as computer readable instructions, data structures, program modules, or other data. For example, computer storage media may comprise RAM, ROM, EEPROM, flash memory or other memory technology, CD-ROM, digital versatile disks (DVD) or other optical storage, magnetic cassettes, magnetic tape, magnetic disk storage or other magnetic storage devices, or any other medium which can be used to store the desired information and which can be accessed by a computer.

The methods and systems can employ artificial intelligence (AI) techniques such as machine learning and iterative learning. Examples of such techniques comprise, but are not limited to, expert systems, case based reasoning, Bayesian networks, behavior based AI, neural networks, fuzzy systems, evolutionary computation (e.g. genetic algorithms), swarm intelligence (e.g. ant algorithms), and hybrid intelligent systems (e.g. Expert inference rules generated through a neural network or production rules from statistical learning).

While specific configurations have been described, it is not intended that the scope be limited to the particular configurations set forth, as the configurations herein are intended in all respects to be possible configurations rather than restrictive.

Unless otherwise expressly stated, it is in no way intended that any method set forth herein be construed as requiring that its steps be performed in a specific order. Accordingly, where a method claim does not actually recite an order to be followed by its steps or it is not otherwise specifically stated in the claims or descriptions that the steps are to be limited to a specific order, it is no way intended that an order be inferred, in any respect. This holds for any possible non-express basis for interpretation, including: matters of logic with respect to arrangement of steps or operational flow; plain meaning derived from grammatical organization or punctuation; the number or type of configurations described in the specification.

It will be apparent to those skilled in the art that various modifications and variations may be made without departing from the scope or spirit. Other configurations will be apparent to those skilled in the art from consideration of the specification and practice described herein. It is intended that the specification and described configurations be considered as exemplary only, with a true scope and spirit being indicated by the following claims.

What is claimed is:

1. A computer program product comprising non-transitory computer memory comprising one or more computer programs configured to perform the steps of:
    receiving, by a device, an electrocardiogram (ECG) signal associated with a patient, wherein the ECG signal comprises one or more artifacts;
    determining, based on the ECG signal, a PSD of the ECG signal;
    determining, based on the PSD, a plurality of highest peaks where each peak has a frequency and a magnitude;
    determining, based on the plurality of highest peaks, a fundamental peak having a fundamental frequency in a 1-3 Hz frequency band and a fundamental magnitude greater than the magnitude of any other peak in the 1-3 Hz frequency band in the plurality of peaks;
    determining, based on the fundamental frequency, a first stop-band filter;
    determining, based on an application of the first stop-band filter to the ECG signal, a filtered ECG signal;
    determining, based on the plurality of highest peaks, a first condition whether any of the peaks other than the fundamental peak in the plurality of peaks is a second peak having a second frequency that is divisible by the fundamental frequency;
    determining a second condition associated with the filtered ECG signal whether a spectral power in a 10-15 Hz frequency band is greater than a threshold;
    determining a third condition associated with the filtered ECG signal threshold whether the second frequency is outside a 3-6 Hz frequency band;
    determining, based on the first condition being satisfied and either the second condition being satisfied or the third condition being satisfied, and based on the second frequency, a second stop-band filter;
    determining, based on an application of the second stop-band filter to the filtered ECG signal, a modified ECG signal; and
    determining, based on the modified ECG signal, to initiate a shock to the patient.

2. The computer program product of claim 1, wherein the ECG signal is received from one or more defibrillation pads affixed to one or more locations of the patient.

3. The computer program product of claim 1, wherein the one or more artifacts are associated with cardiopulmonary resuscitation (CPR) being performed on the patient.

4. The computer program product of claim 1, wherein the modified ECG signal comprises an attenuated signal comprising a suppressed artifact signal.

5. The computer program product of claim 1, wherein determining, based on the modified ECG signal, to initiate the shock to the patient comprises:
    determining, based on the modified ECG signal, a classification associated with a heart rhythm of the patient; and
    determining, based on the classification, to initiate the shock to the patient.

6. The computer program product of claim 5, wherein the classification is indicative of a shockable heart rhythm.

7. The computer program product of claim 1, further comprising causing, based on the determination to initiate the shock, an alert to be output.

8. The computer program product of claim 1, further comprising causing, based on the determination to initiate the shock, the shock to the patient.

9. A processing system comprising a computer processor and the computer program product of claim 1.

10. A computer program product comprising non-transitory computer memory comprising one or more computer programs configured to perform the steps of:
    receiving, by a device, an electrocardiogram (ECG) signal associated with a patient, wherein the ECG signal comprises one or more artifacts;
    determining, based on the ECG signal, a PSD of the ECG signal;
    determining, based on the PSD, a plurality of highest peaks where each peak has a frequency and a magnitude;
    determining, based on the plurality of highest peaks, a fundamental peak having a fundamental frequency in a 1-3 Hz frequency band and a fundamental magnitude greater than the magnitude of any other peak in the 1-3 Hz frequency band in the plurality of peaks;

determining, based on the fundamental frequency, a stop-band filter;
determining, based on an application of the stop-band filter to the ECG signal, a filtered ECG signal;
determining, based on the plurality of highest peaks, a first condition whether any of the peaks other than the fundamental peak in the plurality of peaks is a second peak having a second frequency that is divisible by the fundamental frequency;
determining a second condition associated with the filtered ECG signal whether a spectral power in a 10-15 Hz frequency band is greater than a threshold;
determining a third condition associated with the filtered ECG signal threshold whether, if the first condition is satisfied, the second frequency is outside a 3-6 Hz frequency band;
determining a fourth condition whether, if the first condition is not satisfied, the fundamental frequency is less than 1.5 Hz;
determining, based on either both the second condition and the third condition being satisfied or both the second condition and the fourth condition being satisfied, a modified ECG signal; and
determining, based on the modified ECG signal, to initiate a shock to the patient.

11. The computer program product of claim 10, wherein the ECG signal is received from one or more defibrillation pads affixed to one or more locations of the patient.

12. The computer program product of claim 10, wherein the one or more artifacts are associated with cardiopulmonary resuscitation (CPR) being performed on the patient.

13. The computer program product of claim 10, wherein, the modified ECG signal comprises the filtered ECG signal.

14. The computer program product of claim 10, wherein the modified ECG signal comprises an attenuated signal comprising a suppressed artifact signal.

15. The computer program product of claim 10, wherein determining, based on the modified ECG signal, to initiate the shock to the patient comprises:
determining, based on the modified ECG signal, a classification associated with a heart rhythm of the patient; and
determining, based on the classification, to initiate the shock to the patient.

16. The computer program product of claim 15, wherein the classification is indicative of a shockable heart rhythm.

17. The computer program product of claim 10, further comprising causing, based on the determination to initiate the shock, an alert to be output.

18. The computer program product of claim 10, further comprising causing, based on the determination to initiate the shock, the shock to the patient.

19. A processing system comprising a computer processor and the computer program product of claim 10.

20. A computer program product comprising non-transitory computer memory comprising one or more computer programs configured to perform the steps of:
receiving, by a device, an electrocardiogram (ECG) signal associated with a patient, wherein the ECG signal comprises one or more artifacts;
determining, based on the ECG signal, a PSD of the ECG signal;
determining, based on the PSD, a plurality of highest peaks where each peak has a frequency and a magnitude;
determining, based on the plurality of highest peaks, a fundamental peak having a fundamental frequency in a 1-3 Hz frequency band and a fundamental magnitude greater than the magnitude of any other peak in the 1-3 Hz frequency band in the plurality of peaks;
determining, based on the fundamental frequency, a first stop-band filter;
determining, based on an application of the first stop-band filter to the ECG signal, a filtered ECG signal;
determining, based on the plurality of highest peaks, a first condition whether any of the peaks other than the fundamental peak in the plurality of peaks is a second peak having a second frequency that is divisible by the fundamental frequency;
determining a second condition associated with the filtered ECG signal whether a spectral power in a 10-15 Hz frequency band is greater than a threshold;
determining a fourth condition whether the fundamental frequency is less than 1.5 Hz;
determining, based on the first condition not being satisfied and either the second condition being satisfied or the fourth condition being satisfied, and based on a third frequency that is double the fundamental frequency, a third band-stop filter,
determining, based on an application of the third stop-band filter to the filtered ECG signal, a modified ECG signal; and
determining, based on the modified ECG signal, to initiate a shock to the patient.

21. The computer program product of claim 20, wherein the ECG signal is received from one or more defibrillation pads affixed to one or more locations of the patient.

22. The computer program product of claim 20, wherein the one or more artifacts are associated with cardiopulmonary resuscitation (CPR) being performed on the patient.

23. The computer program product of claim 20, wherein the modified ECG signal comprises an attenuated signal comprising a suppressed artifact signal.

24. The computer program product of claim 20, wherein determining, based on the modified ECG signal, to initiate the shock to the patient comprises:
determining, based on the modified ECG signal, a classification associated with a heart rhythm of the patient; and
determining, based on the classification, to initiate the shock to the patient.

25. The computer program product of claim 24, wherein the classification is indicative of a shockable heart rhythm.

26. The computer program product of claim 20, further comprising causing, based on the determination to initiate the shock, an alert to be output.

27. The computer program product of claim 20, further comprising causing, based on the determination to initiate the shock, the shock to the patient.

28. The computer program product of claim 20 wherein the threshold is 0.07 Watt/Hz.

29. The computer program product of claim 20 wherein the plurality of highest peaks consists of 3 peaks.

30. A processing system comprising a computer processor and the computer program product of claim 20.

* * * * *